(12) United States Patent
Durgin et al.

(10) Patent No.: US 10,952,725 B2
(45) Date of Patent: *Mar. 23, 2021

(54) THROUGH THE SCOPE TENSION MEMBER RELEASE CLIP

(71) Applicants: BOSTON SCIENTIFIC SCIMED, INC., Maple Grove, MN (US); Theresa A. Durgin, Bellingham, MA (US)

(72) Inventors: Russell F. Durgin, Bellingham, MA (US); William C. Mers Kelly, Crestwood, KY (US); Lance Alan Wolf, Madison, AL (US); Brian Keith Wells, LaGrange, KY (US); Vasiliy P. Abramov, Louisville, KY (US); Gregory R. Furnish, Louisville, KY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 399 days.

This patent is subject to a terminal disclaimer.

(21) Appl. No.: 15/962,705

(22) Filed: Apr. 25, 2018

(65) Prior Publication Data

US 2018/0235608 A1    Aug. 23, 2018

Related U.S. Application Data

(60) Continuation of application No. 15/159,512, filed on May 19, 2016, now Pat. No. 9,980,725, which is a
(Continued)

(51) Int. Cl.
*A61B 17/068* (2006.01)
*A61B 17/122* (2006.01)
(Continued)

(52) U.S. Cl.
CPC ........ *A61B 17/0682* (2013.01); *A61B 17/083* (2013.01); *A61B 17/122* (2013.01);
(Continued)

(58) Field of Classification Search
CPC ........ A61B 1/1227; A61B 34/71; A61B 34/76
(Continued)

(56) References Cited

U.S. PATENT DOCUMENTS 3,958,576 A * 5/1976 Komiya ............... A61B 17/083
606/142
5,749,881 A * 5/1998 Sackier ............. A61B 17/1285
606/151
(Continued)

FOREIGN PATENT DOCUMENTS

WO    03/030746    4/2003

*Primary Examiner* — Matthew J Kasztejna
(74) *Attorney, Agent, or Firm* — Fay Kaplun & Marcin, LLP

(57) ABSTRACT

A hemostatic clip assembly for mounting on a delivery device comprises a capsule and a clip slidably mounted within the capsule so that, when the clip is drawn proximally into the capsule, arms of the clip are drawn together to a closed position, an abutting surface of at least one of the arms contacting a corresponding surface of the capsule when the clip is drawn to a predetermined position within the capsule to provide a first user feedback indicating closure of the clip in combination with a tension member connected to the clip arms and biasing the clip arms toward an open, tissue receiving configuration and a yoke slidably received within the capsule and releasably coupled to the tension member, the yoke including a ball cavity for receiving a ball connector of a control element of the delivery device to maintain the clip assembly coupled to the delivery device, wherein the control element is frangible to detach the yoke from the delivery device and to provide a second user
(Continued)

feedback and, wherein release of the yoke from the tension member provides a third user feedback.

14 Claims, 28 Drawing Sheets

Related U.S. Application Data continuation of application No. 14/642,159, filed on Mar. 9, 2015, now Pat. No. 9,370,371, which is a continuation of application No. 13/328,171, filed on Dec. 16, 2011, now Pat. No. 8,974,371, which is a continuation of application No. 12/252,630, filed on Oct. 16, 2008, now Pat. No. 8,083,668, which is a division of application No. 10/955,624, filed on Sep. 30, 2004, now Pat. No. 7,452,327, which is a continuation-in-part of application No. 10/674,512, filed on Sep. 30, 2003, now Pat. No. 7,494,461.

(60) Provisional application No. 60/568,418, filed on May 5, 2004.

(51) Int. Cl.
| | | |
|---|---|---|
| *A61B 17/128* | (2006.01) | |
| *A61B 17/12* | (2006.01) | |
| *A61B 34/00* | (2016.01) | |
| *A61B 17/08* | (2006.01) | |
| *A61B 17/00* | (2006.01) | |
| *A61B 17/29* | (2006.01) | |
| *A61B 90/00* | (2016.01) | |

(52) U.S. Cl.
CPC .......... *A61B 17/1285* (2013.01); *A61B 34/71* (2016.02); *A61B 34/76* (2016.02); *A61B 17/1227* (2013.01); *A61B 2017/003* (2013.01); *A61B 2017/00845* (2013.01); *A61B 2017/00849* (2013.01); *A61B 2017/12004* (2013.01); *A61B 2017/292* (2013.01); *A61B 2034/715* (2016.02); *A61B 2090/034* (2016.02); *A61B 2090/037* (2016.02); *A61B 2090/038* (2016.02)

(58) Field of Classification Search
USPC .......... 600/104; 606/139, 142, 151, 157–158
See application file for complete search history.

(56) References Cited

U.S. PATENT DOCUMENTS

| | | | | |
|---|---|---|---|---|
| 5,766,189 | A * | 6/1998 | Matsuno | A61B 17/122 |
| | | | | 606/139 |
| 7,223,271 | B2 * | 5/2007 | Muramatsu | A61B 17/1227 |
| | | | | 606/139 |
| 8,685,048 | B2 * | 4/2014 | Adams | A61B 17/083 |
| | | | | 606/157 |
| 2002/0045909 | A1 | 4/2002 | Kimura et al. | |
| 2002/0133178 | A1 | 9/2002 | Muramatsu et al. | |

* cited by examiner

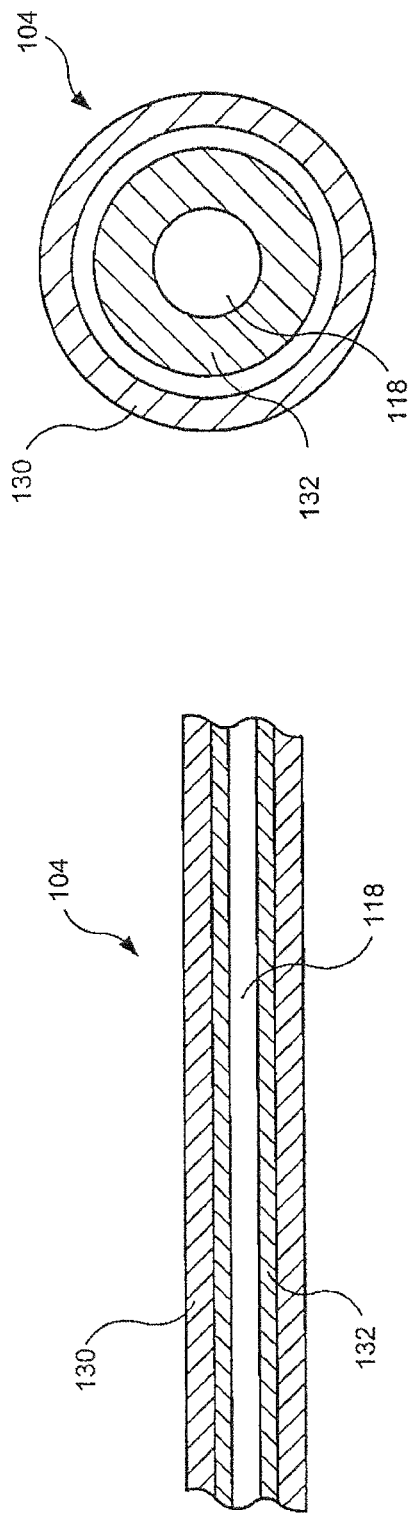
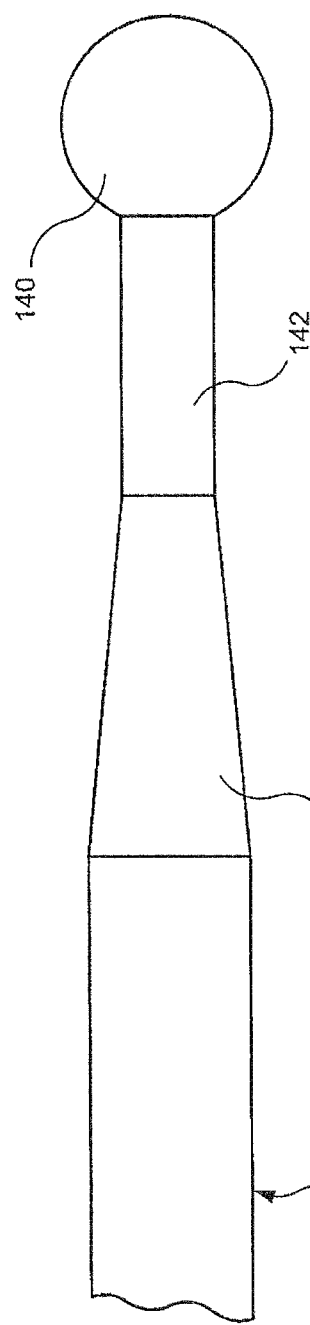

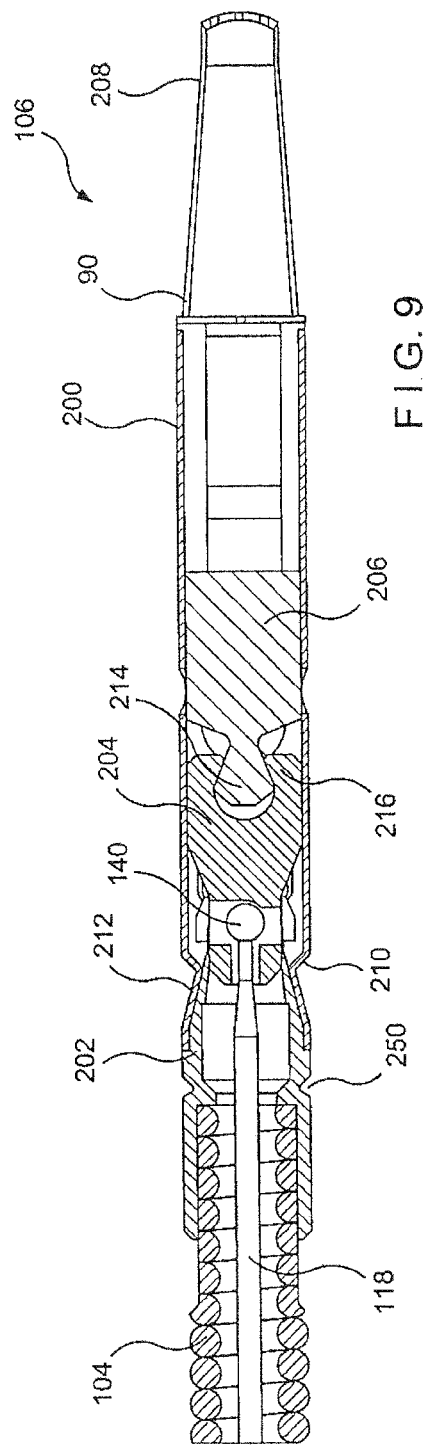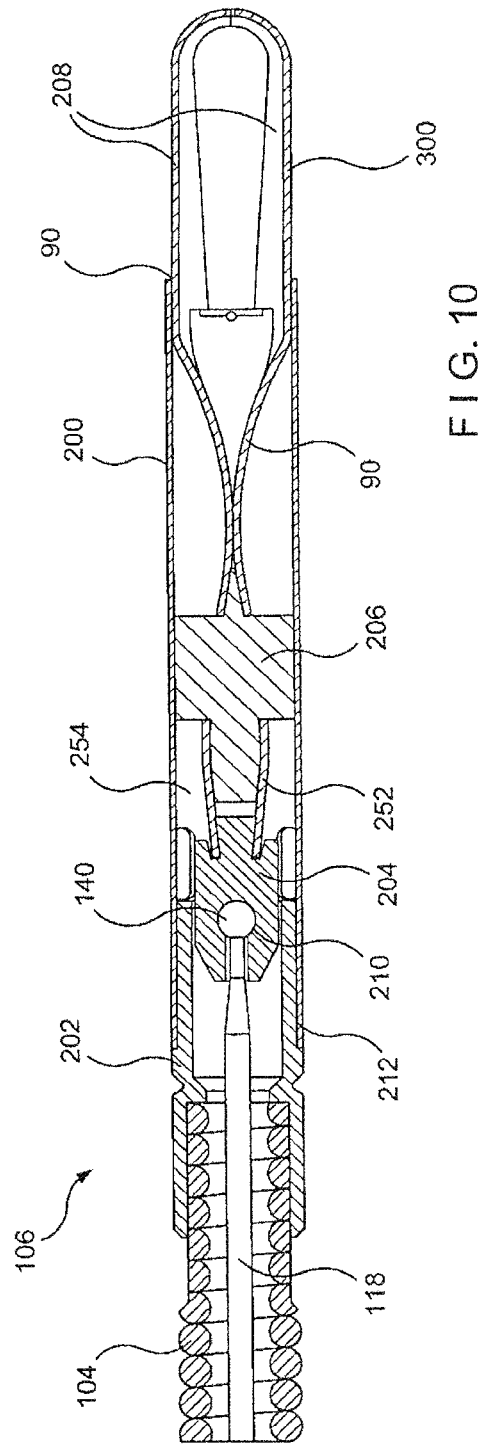

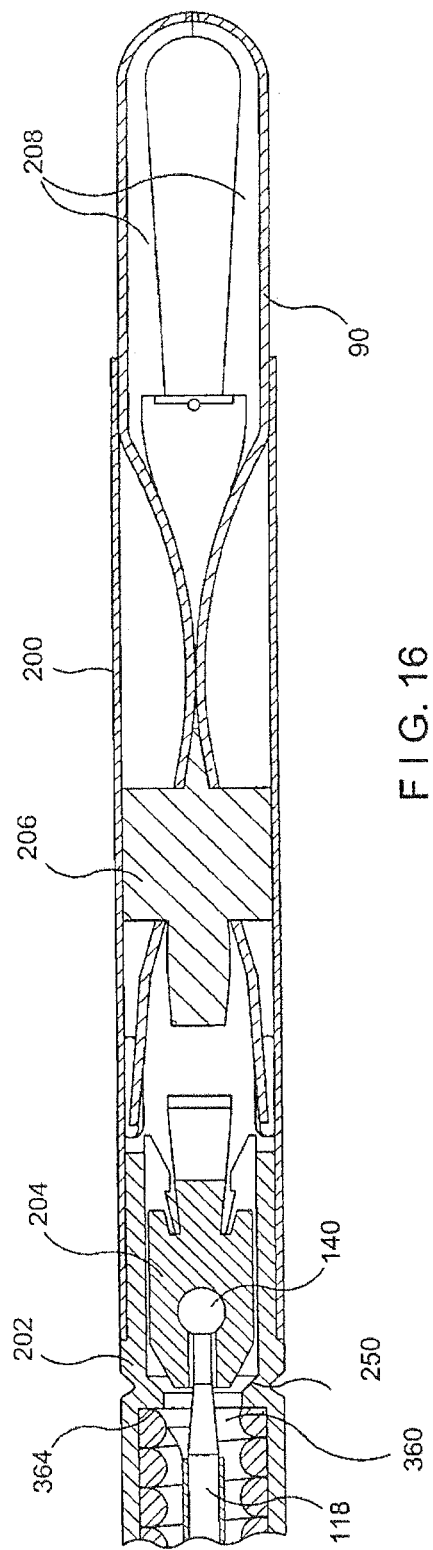
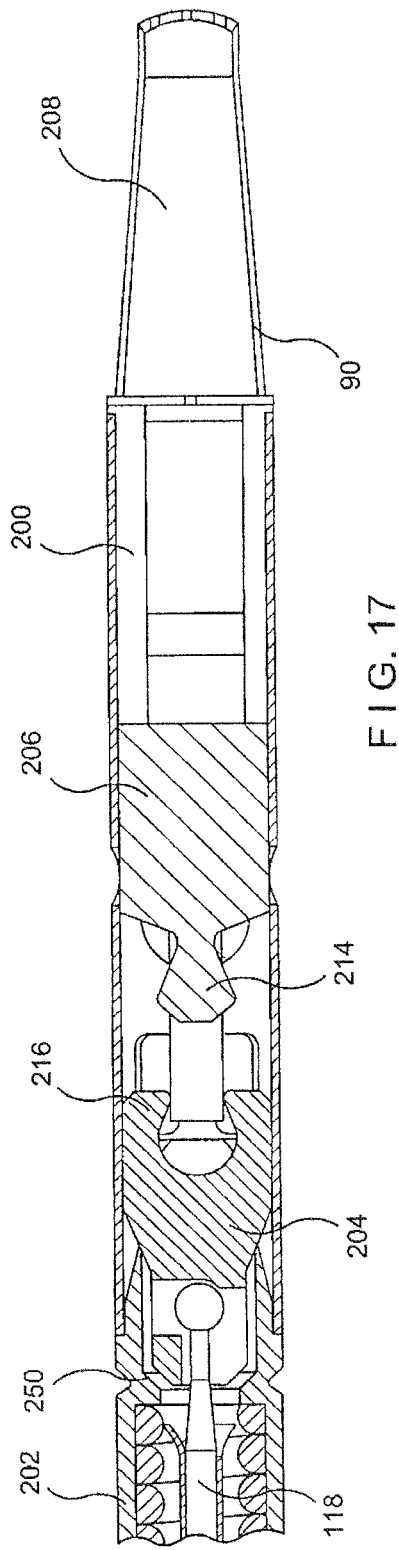
FIG. 16
FIG. 17

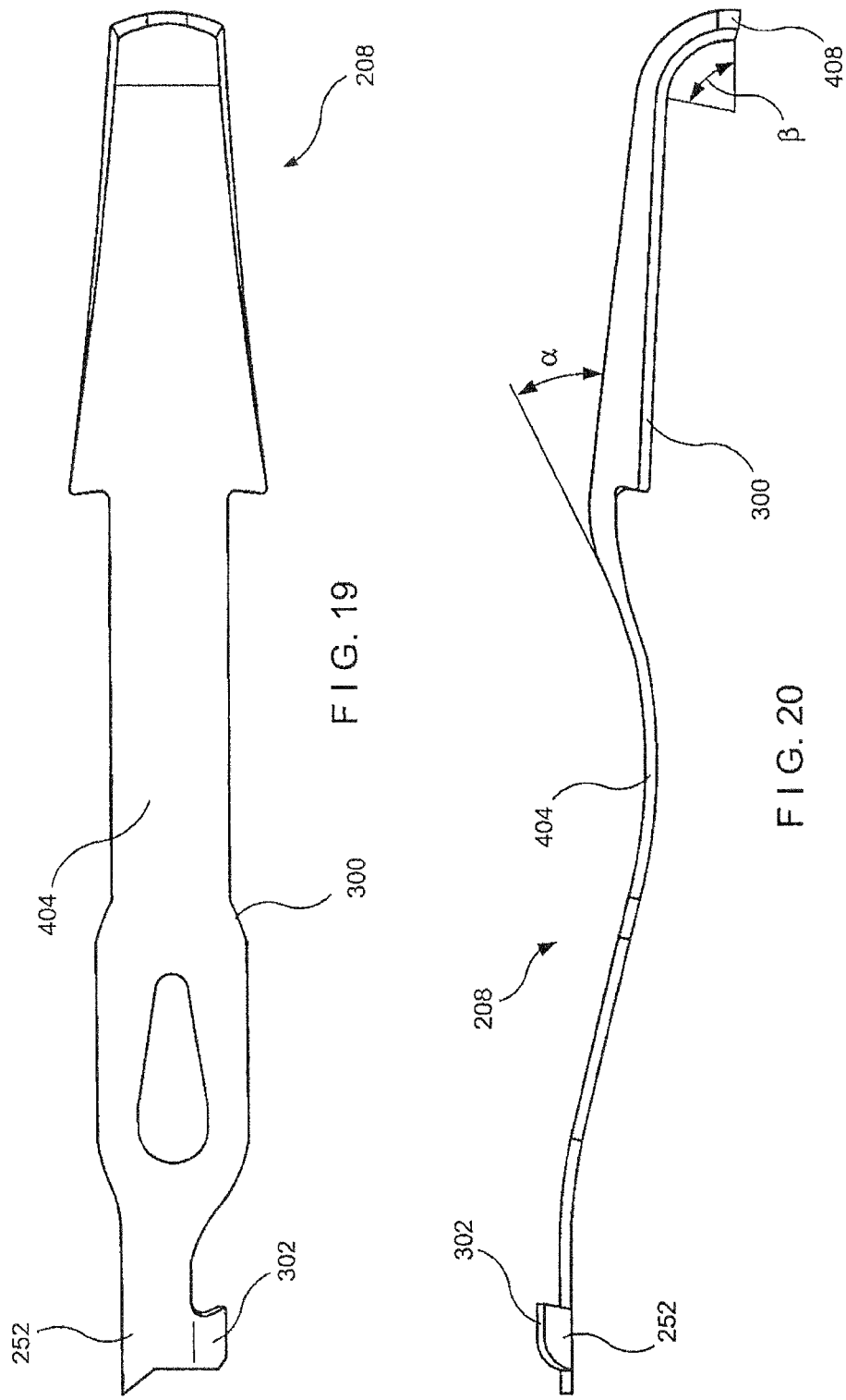

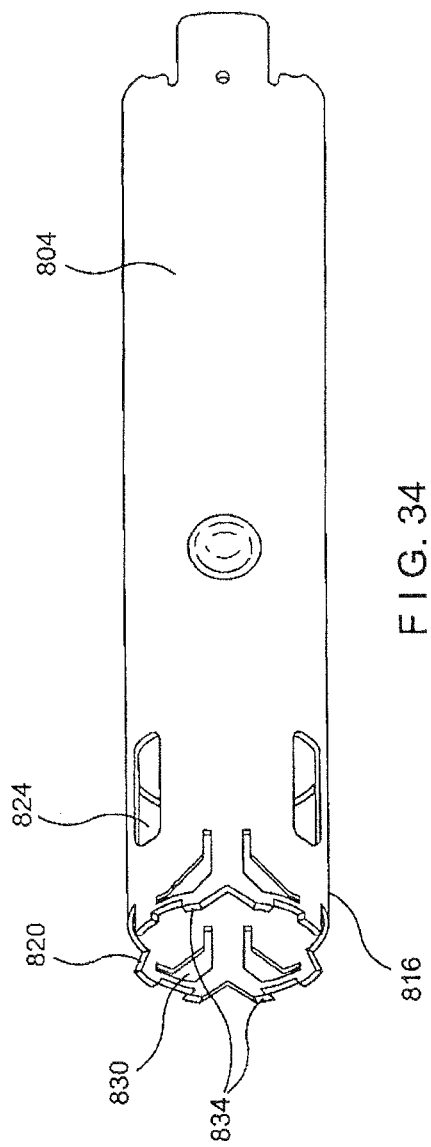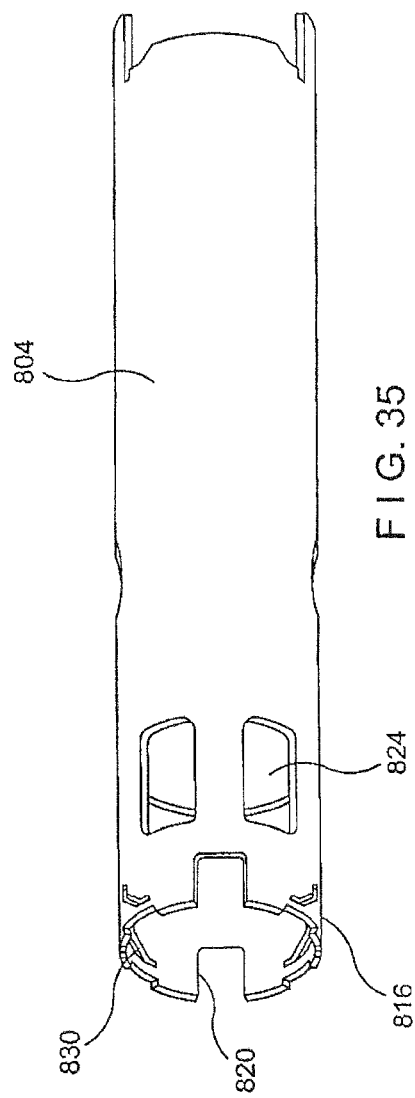

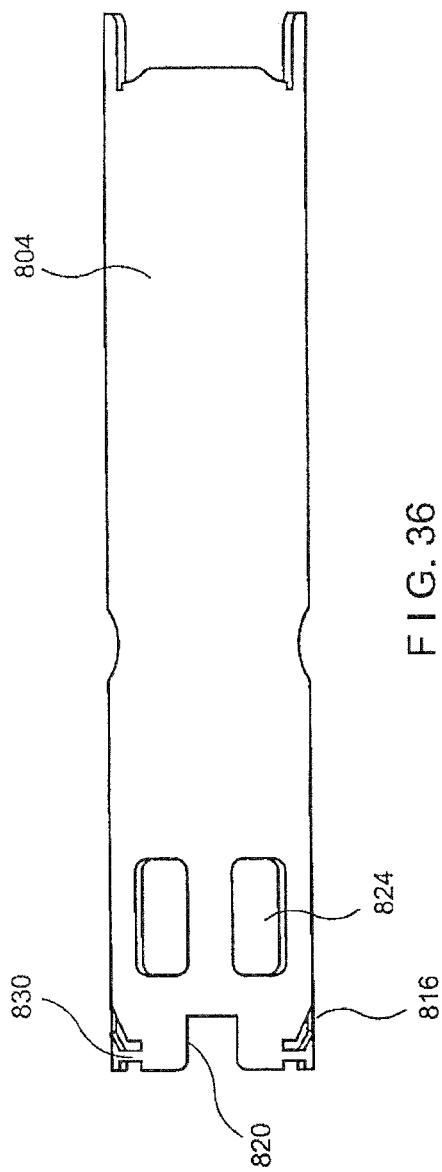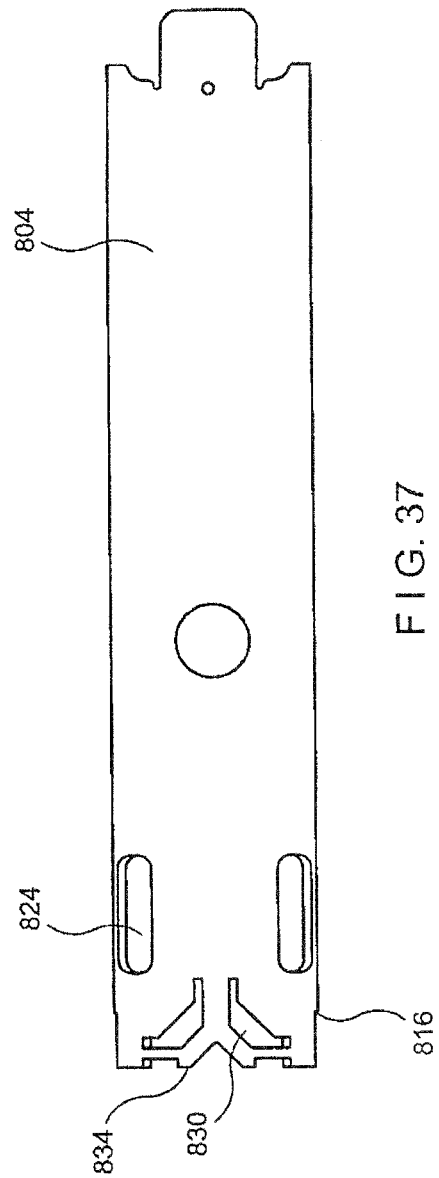
FIG. 36
FIG. 37

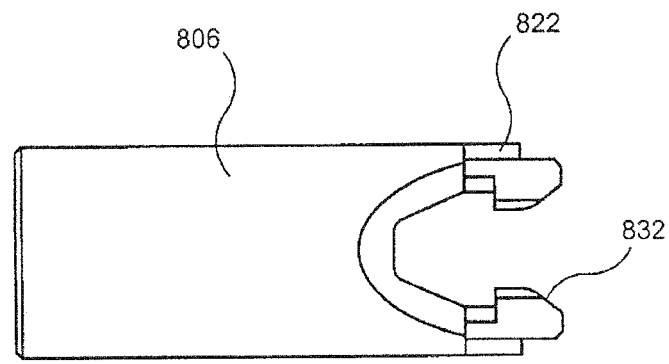
F I G. 38
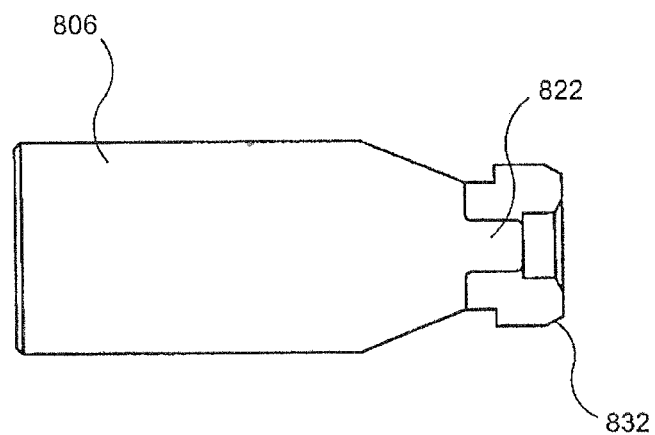
F I G. 39

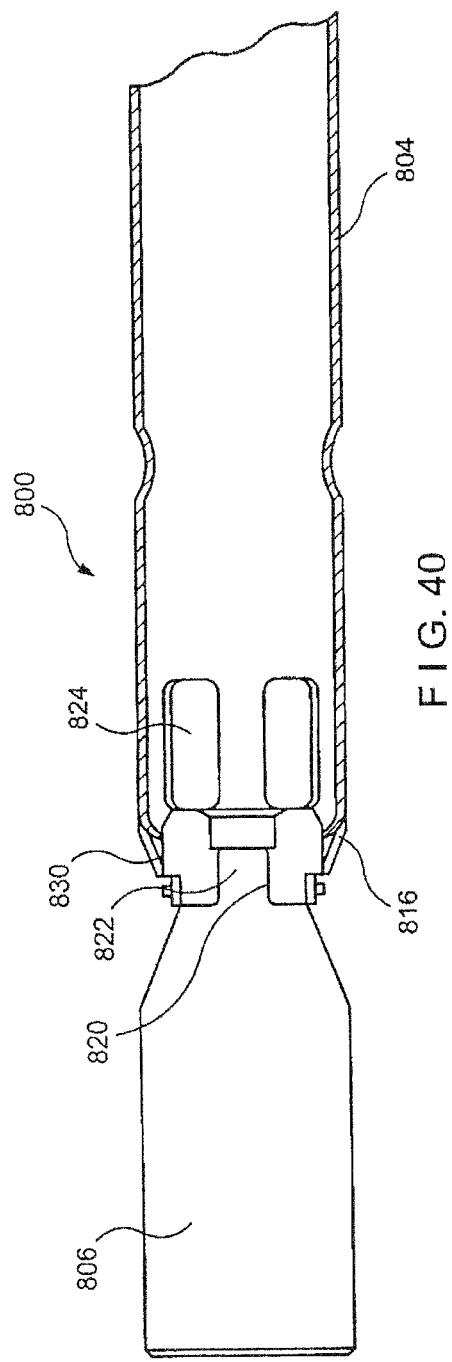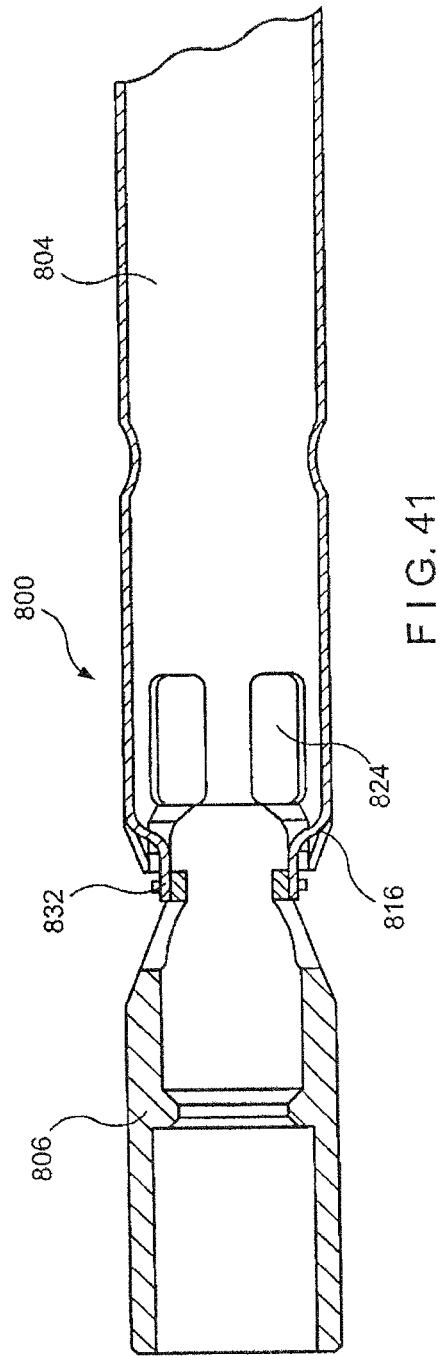

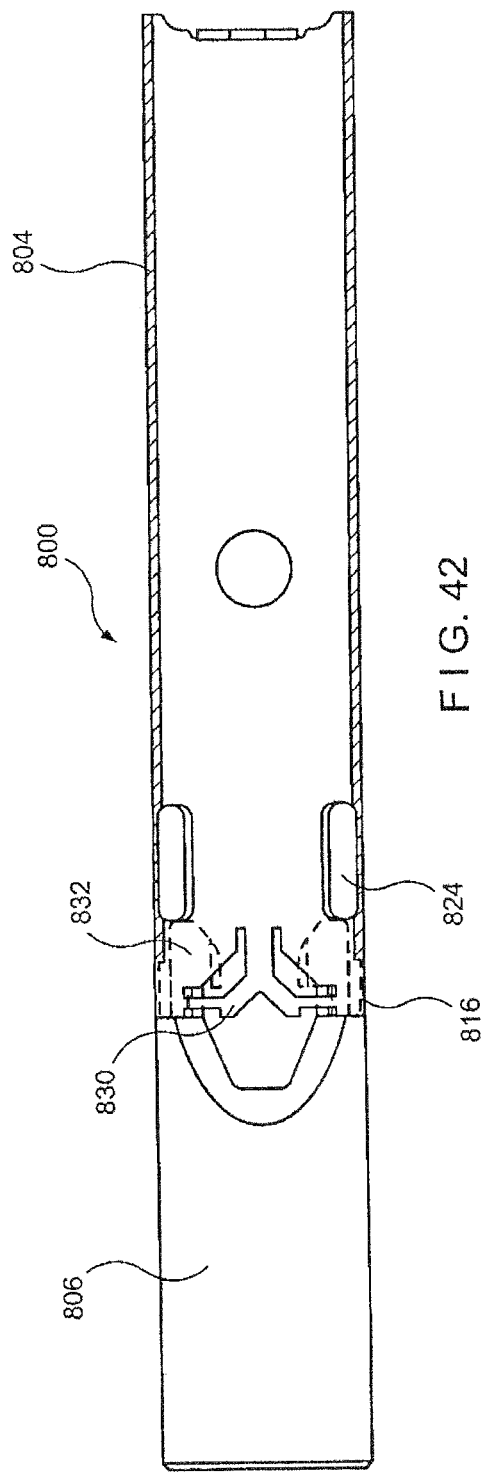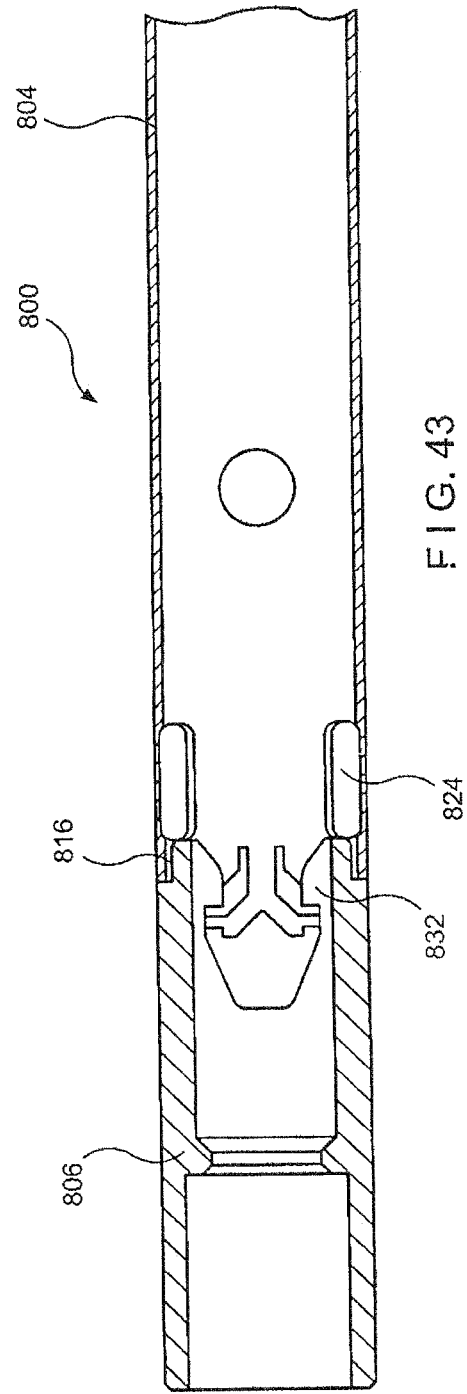

THROUGH THE SCOPE TENSION MEMBER RELEASE CLIP

PRIORITY CLAIM

The present application is a Continuation of U.S. patent application Ser. No. 15/159,512 filed on May 19, 2016, now U.S. Pat. No. 9,980,725; which is a Continuation of U.S. patent application Ser. No. 14/642,159 filed on Mar. 9, 2015, now U.S. Pat. No. 9,370,371; which is a Continuation of U.S. patent application Ser. No. 13/328,171 filed on Dec. 16, 2011, now U.S. Pat. No. 8,974,371; which is a Continuation of U.S. patent application Ser. No. 12/252,630 filed on Oct. 16, 2008, now U.S. Pat. No. 8,083,668 which is a Divisional application of U.S. patent application Ser. No. 10/955,624 filed on Sep. 30, 2004, now U.S. Pat. No. 7,452,327, which (A) is a Continuation-in-Part of U.S. patent application Ser. No. 10/674,512 filed on Sep. 30, 2003, now U.S. Pat. No. 7,494,461 and (B) claims priority to U.S. Provisional Patent Application Ser. No. 60/568,418 filed on May 5, 2004. All applications/patents are expressly incorporated herein, in their entirety, by reference.

BACKGROUND

Endoscopic procedures to treat pathologies of the gastro-intestinal ("GI") system, the biliary tree, the vascular system and of other body lumens are becoming increasingly common.

Hemostatic clipping tools have been inserted through endoscopes to deploy hemostatic clips which stop internal bleeding by clamping together the edges of a wound. Such a clipping tool, complete with clips attached to a distal end thereof, may be inserted through an endoscope to the location of bleeding. A clip is then remotely manipulated into position over the site of the bleeding, clamped over the wound and detached from the tool.

One challenge facing the endoscope operator is to properly position the hemostatic clips over the wound to effectively stop the bleeding. If a clip is deployed improperly, additional clips may be required to stop the bleeding, extending the time required for and the complexity of the procedure and leaving additional medical devices within the patient. It is also important for the device operator to be certain of the status of deployed clips during the deployment operation. For example, before withdrawing the tool from the endoscope, the operator should have positive indication that all of the deployed clips have been fully deployed and completely released from the tool to prevent a clip which is clamped on tissue yet cannot be released from the tool.

SUMMARY OF THE INVENTION

In one aspect, the present invention is directed to a hemostatic clip assembly for mounting on a delivery device comprising a capsule and a clip slidably mounted within the capsule so that, when the clip is drawn proximally into the capsule, arms of the clip are drawn together to a closed position, an abutting surface of at least one of the arms contacting a corresponding surface of the capsule when the clip is drawn to a predetermined position within the capsule to provide a first user feedback indicating closure of the clip in combination with a tension member connected to the clip arms and biasing the clip arms toward an open, tissue receiving configuration and a yoke slidably received within the capsule and releasably coupled to the tension member, the yoke including a ball cavity for receiving a ball connector of a control element of the delivery device to maintain the clip assembly coupled to the delivery device, wherein the control element is frangible to detach the yoke from the delivery device and to provide a second user feedback and, wherein release of the yoke from the tension member provides a third user feedback.

BRIEF DESCRIPTION OF THE DRAWINGS

FIG. 1A is a detail view of an exemplary clip assembly shown in FIG. 1;

FIG. 3 is a cut away side view of the shaft section according to an embodiment of the present invention;

FIG. 4 is a cross sectional view of the shaft section shown in FIG. 3;

FIG. 5 is a detail view of the distal end of the control wire according to an embodiment of the present invention;

FIG. 9 is a cross sectional side view of a distal end of a clipping device according to an embodiment of the present invention;

FIG. 10 is a cross sectional top view of a distal end of the clipping device shown in FIG. 9;

FIG. 16 is a top view of the distal end of a clipping device according to an embodiment of the present invention;

FIG. 17 is a side view of the distal end shown in FIG. 16;

FIG. 19 is a side view of the clip arm shown in FIG. 18;

FIG. 20 is a top view of the clip arm shown in FIG. 18;

FIG. 34 is a perspective view of a clip capsule according to a different embodiment of the invention;

FIG. 35 is another perspective view of the capsule shown in FIG. 34;

FIG. 36 is a side elevation view of the capsule shown in FIG. 34;

FIG. 37 is a top view of the capsule shown in FIG. 34;

FIG. 38 is a top view of a bushing according to a different embodiment of the invention;

FIG. 39 is a side view of the bushing shown in FIG. 38;

FIG. 40 is a partially cross-sectional top view of a bushing-capsule assembly according to a different embodiment of the invention;

FIG. 41 is a cross sectional area of the assembly shown in FIG. 40;

FIG. 42 is a partially cross-sectional side view of the assembly shown in FIG. 40; and FIG. 43 is a cross sectional view of the assembly shown in FIG. 42.

DETAILED DESCRIPTION

Hemostatic clips are used routinely to stop bleeding from openings created during surgery as well as wounds resulting from other trauma to tissues. In the simplest form, these clips grasp the tissue surrounding a wound and bring the wound's edges together to allow natural processes to heal the wound. Endoscopic hemostatic clips are used to stop internal bleeding resulting from surgical procedures and/or tissue damage from disease, etc. Specialized endoscopic hemostatic clipping devices are used to bring the clips to the desired location within a patient's body and to position and deploy the clip at the appropriate place on the tissue. The clipping device is then withdrawn, leaving the clip within the patient.

Endoscopic hemostatic clipping devices are designed to reach affected tissues deep within a patient's body, such as within the GI tract, the pulmonary system, the vascular system or within other lumens and ducts. During the procedures to treat those areas, an endoscope is generally used to provide access to and visualization of the tissue which is to be treated. The clipping device may, for example, be introduced through a working lumen of the endoscope. The design and construction of such a "through the scope" endoscopic hemostatic clipping device presents several challenges. The endoscopic clipping device has to be sufficiently small to fit in the lumen of an endoscope and, at the same time, must be designed to provide for the positive placement and actuation of the hemostatic clip. Feedback to the operator is preferably also provided so that the operator will not be confused as to whether the hemostatic clip has been properly locked in place on the tissue and released from the device before the device itself is withdrawn through the endoscope.

Figure 1:
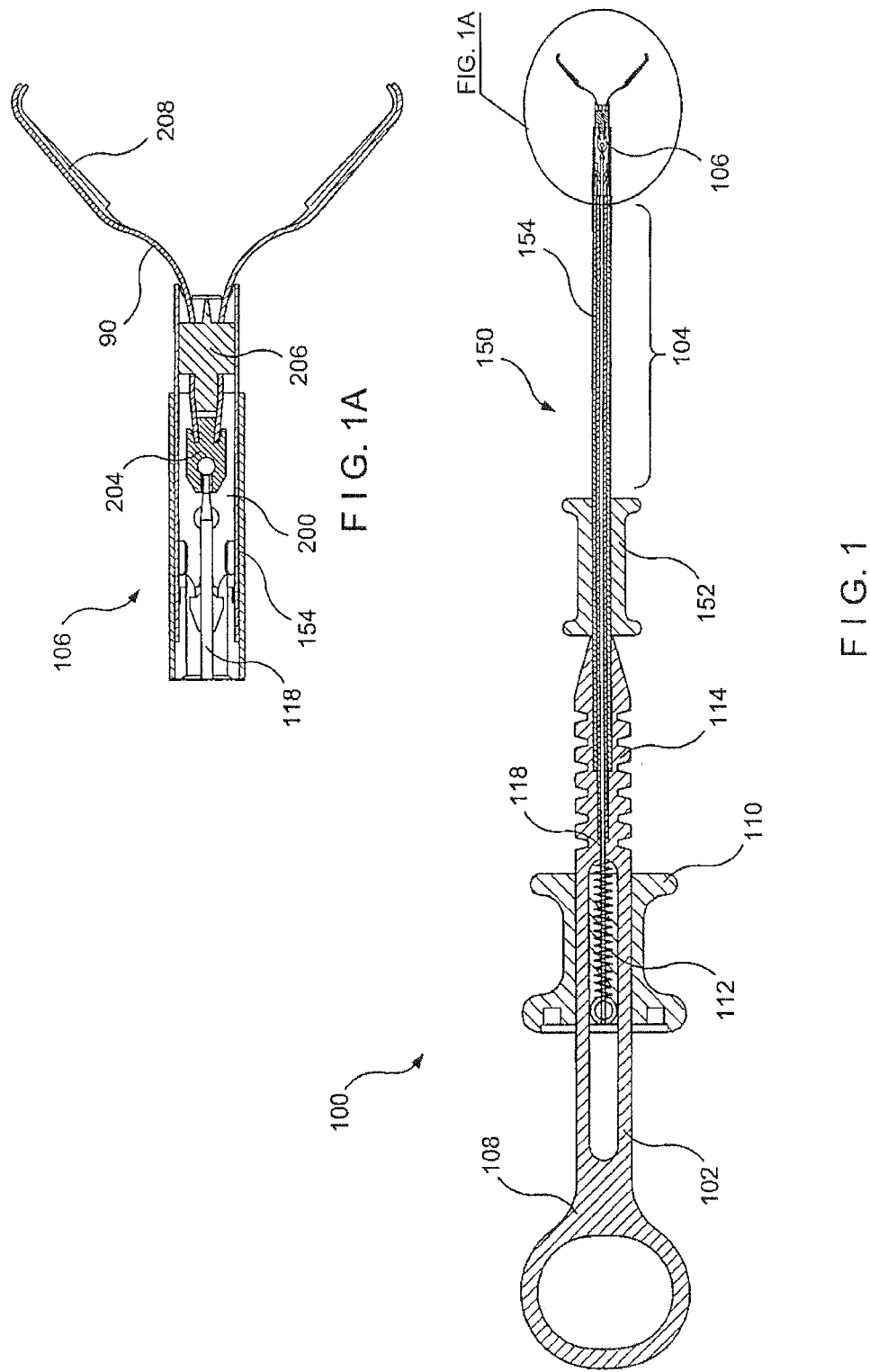
FIG. 1 is a schematic side view of a clipping device according to an embodiment of the present invention.

FIG. 1 shows a side elevation view of a through the scope hemostatic clipping device according to an exemplary embodiment of the present invention. This device is a hand operated tool that is used to insert a hemostatic clip through an endoscope lumen, position the clip over a wound, clamp it and deploy it over the affected tissue. The tool is further designed to release the hemostatic clip once it has been clamped in place, and to be withdrawn through the endoscope. To more clearly explain the operation and construction of the exemplary device, it may be divided into three principal components. As shown, the hemostatic clipping device 100 comprises a handle assembly 102, a shaft section 104, and a clip assembly 106. The clip assembly 106 is shown more clearly in FIG. 1A.

The handle assembly 102 forms the component that supplies a mechanical actuation force to deploy and clamp the clip. In this embodiment, the device 100 is hand operated (i.e., the user's hands provide the force required to carry out all the functions related to the hemostatic clip). The handle assembly 102 may be constructed in a manner similar to conventional handle assemblies of the type generally employed in endoscopic biopsy devices or in similar applications. The handle assembly 102 allows the user to move a control wire 118 or other force transmission member, which extends through the shaft section 104 to the clip assembly 106 at a distal end of the device 100. The handle assembly 102 comprises a handle body 108 which can be grasped by the user to stabilize the device and apply a force to it. A sliding spool 110 is connected to control wire 118, so that the user can easily pull or push said wire 118 as desired.

Figure 2:
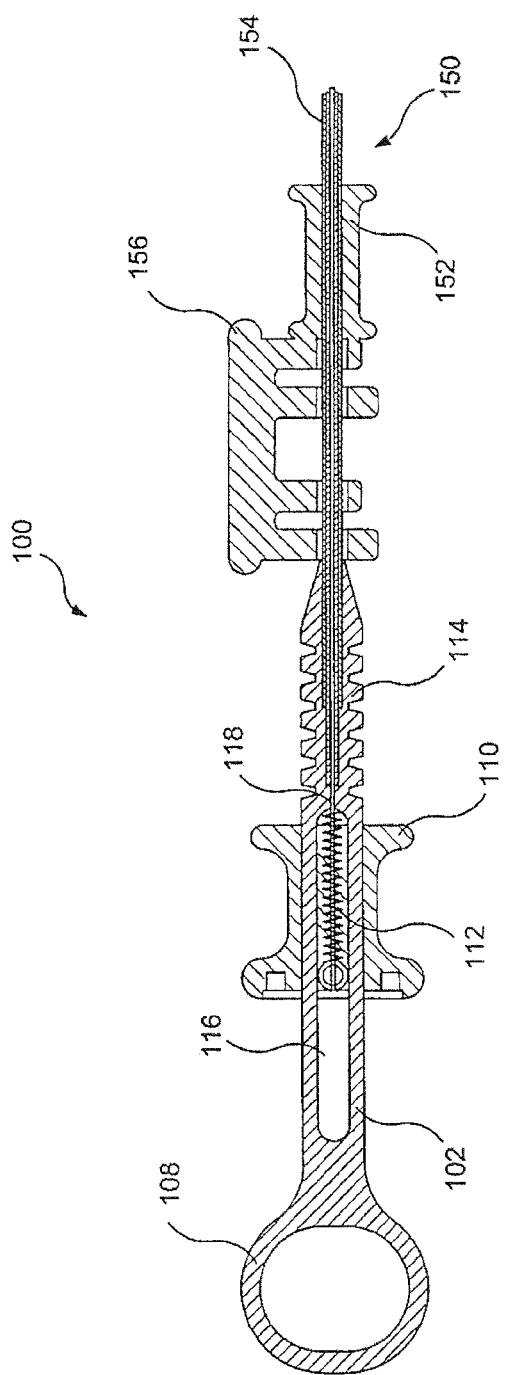
FIG. 2 is a side view of the embodiment shown in FIG. 1, with an outer sheath.

As shown in FIGS. 1 and 2, a sliding spool 110 is mounted on the handle body 108 so that it can slide along a slot 116, which maintains its position within the handle assembly 102. Because the sliding spool 110 is connected to the control wire 118, the user may manipulate the control wire 118 by grasping the handle body 108 and moving the sliding spool 110 along the slot 116. A return spring 112 may be provided within the handle body 108 to bias the sliding spool 110, and thus the control wire 118 toward a desired position. In the present embodiment, the sliding spool 110 is biased to the proximal position. The handle assembly 102 may also include a connection portion 114, which receives the control wire 118 and attaches the shaft section 104 to the handle assembly 102.

The shaft section 104 mechanically connects the handle assembly 102 to the clip assembly 106 and, together with the clip assembly 106, is designed to be inserted into a lumen of an endoscope. As shown in FIGS. 3 and 4, the shaft section 104 comprises an outer flexible coil 130 which is designed to transmit a torque from the proximal end to the distal end of the device 100 and to provide structural strength to the shaft section 104. The coil 130 may be a conventional coil used in biopsy devices and may, for example, comprise a single, coiled wire. The coiled wire may have a round, square or a rectangular cross section, and may be made of a biocompatible material such as, for example, stainless steel. Additional protective and low friction outer layers may be included on the shaft section 104, according to known methods of construction.

The control wire 118 transmits mechanical force applied to the handle 102 to the clip assembly 106. The control wire 118 has a proximal end which is attached to a movable part of the handle 102, such as the sliding spool 110, using known methods. Stainless steel or other high yield biocompatible materials may be used to manufacture the control wire 118, so that the structural integrity of the assembly is maintained. It is also important to prevent stretching of the control wire 118 when under tension since, if the wire stretches, the handle 102 will have to travel a greater distance to carry out a desired operation. As shown in FIG. 5, the distal end of the control wire 118 ends in a ball 140 which is used to connect the control wire 118 to the appropriate elements of the clip assembly 106, as will be described below. In this embodiment, the diameter of the control wire 118 is substantially constant from a proximal end thereof to a proximal end of a distal tapered section 144. The ball 140 may have a diameter which is greater than the diameter of the control wire 118, to facilitate attachment to a yoke 204. The control wire 118 may extend the length of the device 100, from the yoke 204 to the sliding spool 110, and slides longitudinally through the device 100. It may be made, for example, of stainless steel or other biocompatible metal.

The control wire 118 may also include a reduced diameter section 142 designed to fail when a predetermined tension is applied thereto through the handle assembly 102. The tapered section 144 may be used to transition between the main body of the control wire 118 and the reduced diameter section 142, without steps or other discontinuities which may concentrate stress and make the fracture point more unpredictable. As will be described in greater detail below, one purpose of the reduced diameter section 142 is to facilitate the release of a hemostatic clip from the hemostatic clipping device 100 once the clip has been properly deployed. It will be apparent to those of skill in the art that the location of the reduced diameter section 142 along the control wire 118 may be varied to take into account specific requirements of the device 100.

An inner sheath 132 may be used in the construction of the shaft section 104, as shown in FIGS. 3 and 4. The inner sheath 132 provides a low friction bearing surface disposed between the outer diameter of the control wire 118, and the inner diameter of the shaft section 104. The Inner sheath 132 may be formed of a low friction material such as, for example, Teflon™, HDPE or Polypropylene. In one exemplary embodiment, the inner sheath 132 is slidable within the shaft section 104, and the control wire 118 is slidable within the inner sheath 132 forming a low friction system of multiple bearing surfaces. To further reduce friction, a bio-compatible lubricant may be applied to the inner and outer surfaces of the inner sheath 132, along the length of the shaft section 104. For example, silicone lubricants may be used for this purpose.

A slidable over-sheath 150 may be included in the design of the shaft section 104, as shown in FIGS. 1 and 2. The over-sheath 150 is designed to protect the inner lumen of the endoscope from the metal clip assembly 106 and from the metal coil 130 while the hemostatic clipping device 100 passes through the endoscope's lumen. After the clipping device 100 and, more specifically, after the clip assembly 106 has passed through the endoscope, the over-sheath 150 may be withdrawn to expose the distal portion of the clipping device 100. The over-sheath 150 may be formed, for example, as a single lumen plastic extrusion element slidable over the distal portions of the clipping device 100 to selectively cover and uncover the clip assembly 106. In one embodiment, the over-sheath 150 is formed of a low friction polymer such as, for example, Teflon™, HDPE, Polypropylene, or similar materials.

The over-sheath 150 may include a grip portion 152 and an elongated body 154. The grip portion 152 is designed as a handle making it easier for the user to slide the over-sheath 150 over the shaft of the clipping device 100. In one exemplary embodiment, the grip portion 152 is made of a rubber-like material to provide a good gripping surface for the user. For example, an injection moldable polymer such as TPE may be used to construct the grip portion 152. The elongated body 154 may be formed as a substantially cylindrical shell surrounding the shaft of the clipping device 100. The elongated body 154 may be attached to the grip portion 152 using conventional methods as would be understood by those skilled in the art.

Figure 6:
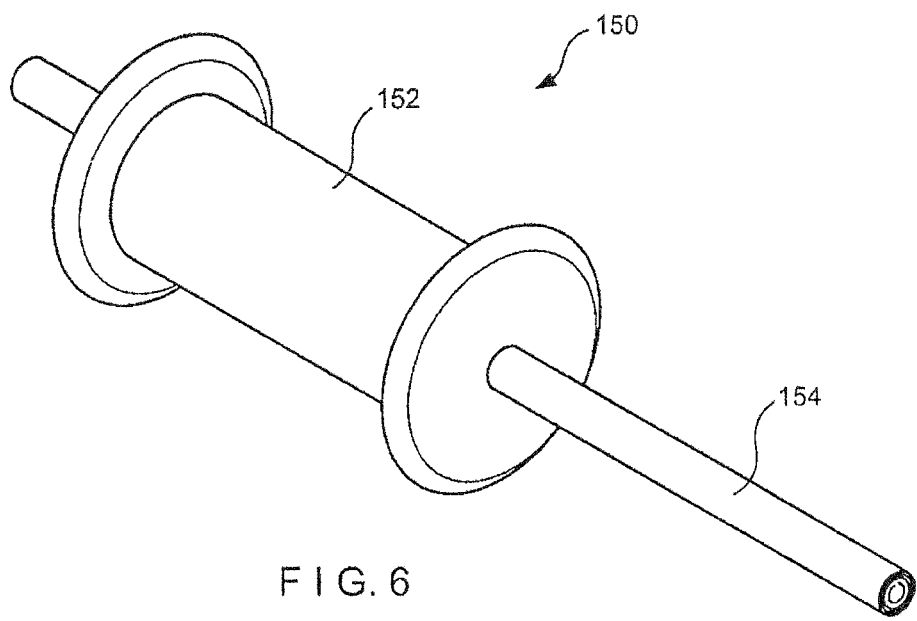
FIG. 6 is a perspective view of an outer sheath according to an embodiment of the present invention.
Figure 7:
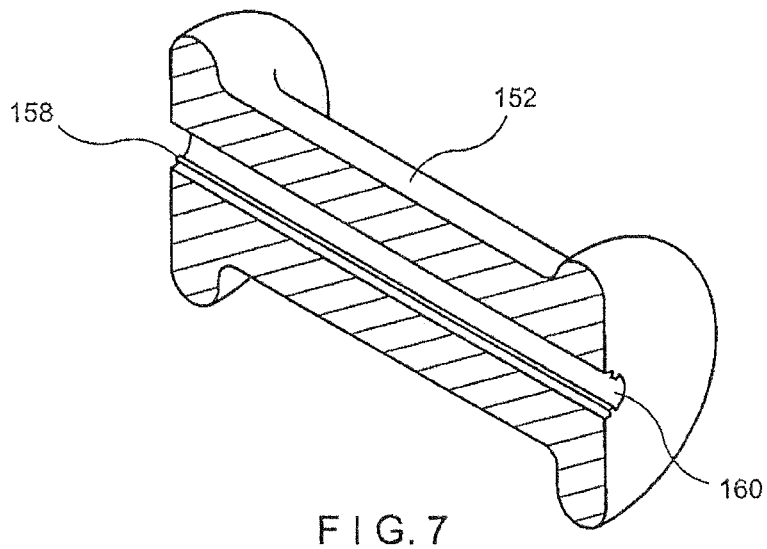
FIG. 7 is a cross sectional exploded view of the handle of the outer sheath shown in FIG. 6.

As shown in FIGS. 6 and 7, an exemplary grip portion 152 comprises a central hollow channel 160 that may be used to receive the shaft of the clipping device 100. The central hollow channel 160 is aligned with the elongated body 154 to provide a continuous channel containing the shaft of the clipping device 100. The material of the grip portion 152 may have a high coefficient of friction, so that an interference fit is possible between the central hollow channel 160 and the shaft of the clipping device 100 without the use of adhesives or mechanical fastening devices. In one embodiment, friction bosses 158 may be provided on an inner diameter of the hollow channel 160 to provide additional friction between the shaft of the clipping device 100 and the over-sheath 150 assembly. The friction bosses 158 may be formed, for example, as protrusions extending from the inner diameter of the over-sheath 150 and may have a variety of stubby or elongated shapes. The amount of friction between these two components may be balanced so that no unwanted relative movement takes place while, at the same time, making it relatively easy for the user to slide the over-sheath 150 proximally and distally when necessary.

Figure 8:
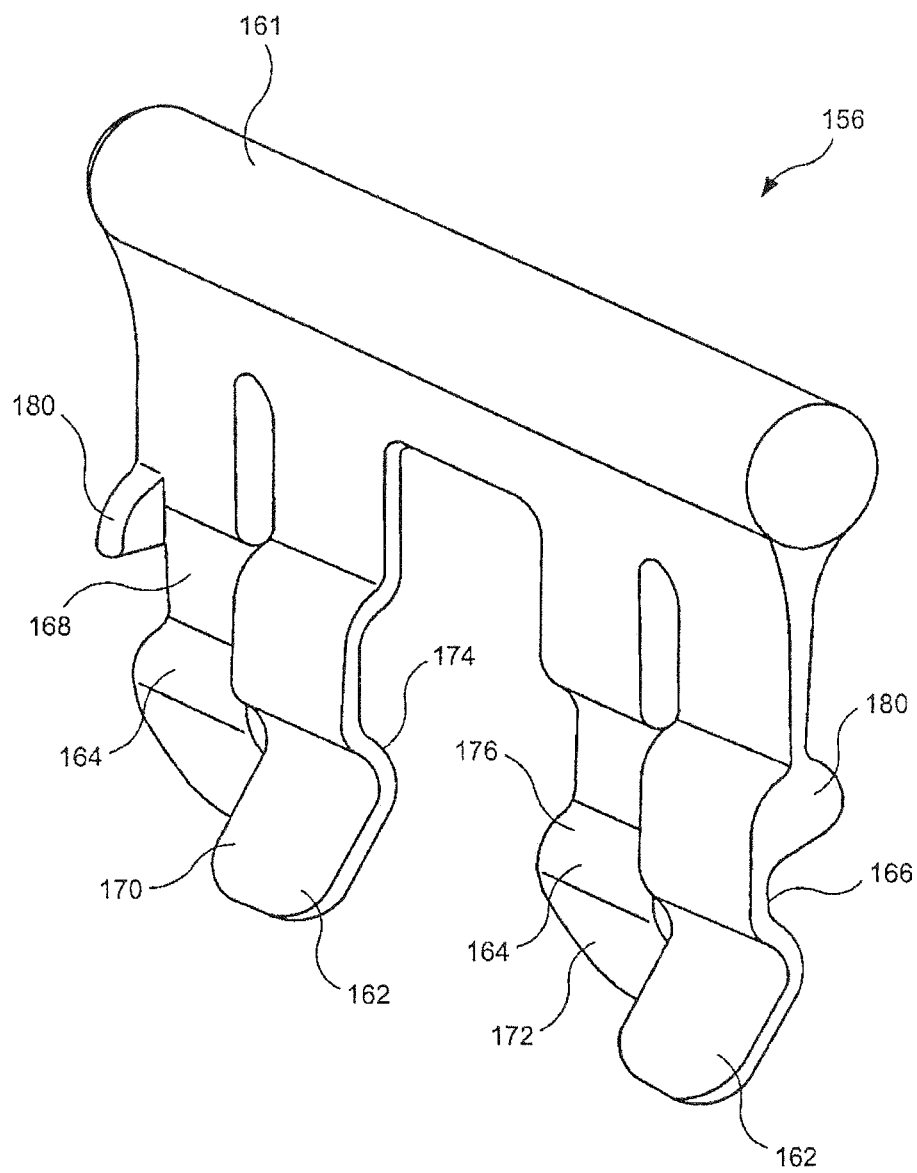
FIG. 8 is a perspective view of an outer sheath lock according to an embodiment of the present invention.

A sheath stop 156 may be provided for the clipping device 100 to prevent the over-sheath 150 from sliding away from the distal end while the clipping device 100 is inserted in the endoscope. As shown in the exemplary embodiment of FIGS. 2 and 8, the sheath stop 156 physically blocks the grip portion 152 from sliding proximally to prevent the over-sheath 150 from being withdrawn and exposing the clip assembly 106. The sheath stop 156 is designed to easily snap in place near the proximal end of the shaft section 104 where it can be reached and manipulated by the operator during the surgical procedure. Once the clip assembly 106 has been inserted in the endoscope and has reached the desired location in the patient's body, the sheath stop 156 may be removed from the shaft section 104 so that the user can move the grip portion 152 proximally to uncover the clip assembly 106.

The connection between the sheath stop 156 and the shaft section 104 may include, for example, pairs of opposing fingers 162, 164 that are designed to snap over the shaft section 104. The fingers 162, 164 cooperate to securely and releasably hold the body of the shaft section 104 therebetween. The fingers 162, 164 respectively comprise guide portions 170, 172; shaft channel portions 166, 168; and blocking portions 174, 176. Insertion of the sheath stop 156 on the elongated body 154 is accomplished by pressing the body of the shaft section 104 between the guide portions 170, 172, to spread the fingers 162, 164 and allow further insertion of the shaft 104 between the fingers 162, 164. The guide portions 170, 172 and the blocking portions 174, 176 are shaped so that insertion of the shaft section 104 towards the channel portions 166, 168 requires less effort than moving the shaft section 104 in the opposite direction.

Once the shaft section 104 has been placed within the channel portions 166, 168, the fingers 162, 164 snap back to their non-spread position and retain the shaft section 104 in place therebetween. The shaft section 104 is removed by pulling the sheath stop 156 away from the shaft section 104. Due to the shape of the blocking portions 174, 176, removing the shaft section 104 requires the application of more force than does insertion thereinto. Stops 180 may also be provided on the sheath stop 156 to limit the movement of the shaft section 104 towards the grasping portion 161 to prevent damage to the device that may be caused by excessive spreading of the fingers 162, 164. The sheath stop 156 may be formed of a resilient material, such as a polymer, and may be manufactured by injection molding.

Figure 11:
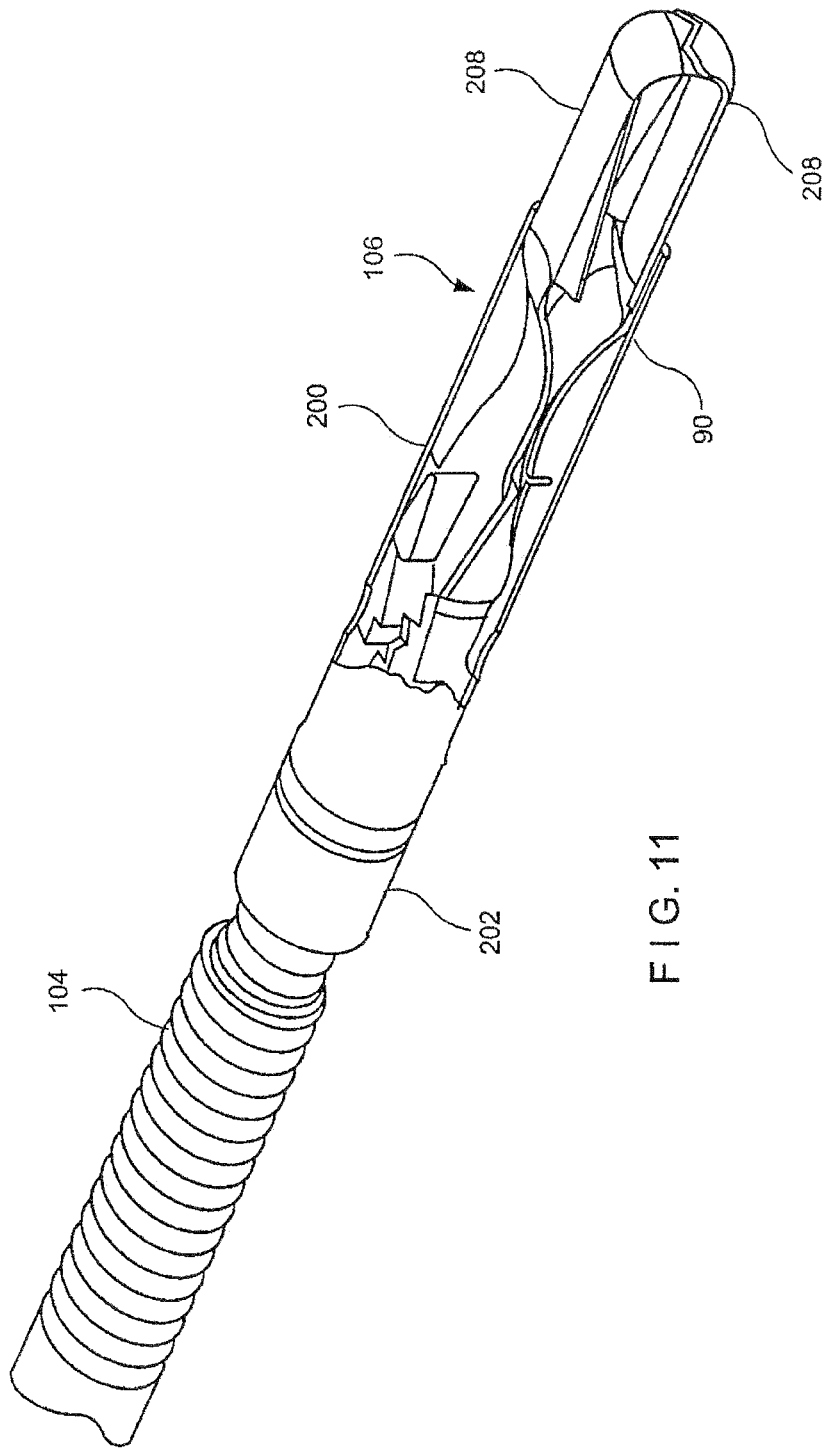
FIG. 11 is a cross-sectional, perspective view of the distal end of the clipping device shown in FIG. 9.

The clip assembly 106 is disposed at the distal end of the clipping device 100, and contains the mechanism that converts the proximal and distal movement of the control wire 118 into the actions necessary to deploy and release a hemostatic clip 90. FIGS. 9, 10 and 11 show, respectively, side, top and perspective views of the distal end of the clipping device 100, including the clip assembly 106 having clips in the folded configuration. This configuration is used, for example, to ship the clipping device 100 and to insert the clipping device 100 through the lumen of an endoscope. Some of the components of the clip assembly 106 include a capsule 200 which provides a structural shell for the clip assembly 106, the clip arms 208 which move between open and closed positions, a bushing 202 attached to the coil 130, and a yoke 204 connecting the control wire ball 140 and the tension member 206.

As depicted in the exemplary embodiment, the proximal end of the capsule 200 slides over the distal end of the bushing 202. A locking arrangement between these two exemplary components is provided by capsule tabs 212, which are designed to lock into the bushing 202 so that mechanical integrity is temporarily maintained between the capsule 200 and the bushing 202. Within the capsule 200 are contained a yoke 204 and a tension member 206 which transmit forces applied by the control wire 118 to the clip arms 208. The ball 140 formed at the distal end of the control wire 118 is mated to a receiving socket 210 formed at the proximal end of the yoke 204. A male C-section 214 extending from the tension member 206 is received in a corresponding female C-section 216 formed in the yoke 204, so that the two components are releasably connected to one another, as will be described below. The clip arms 208 in the closed configuration have a radius section 300 which is partially contained within the capsule 200 to prevent opening of the arms. Each of the clip arms 208 goes over the tension member 206 and has a proximal end 252 which slips under a yoke overhang 254, to further control movement of the arms 208.

Figure 12:
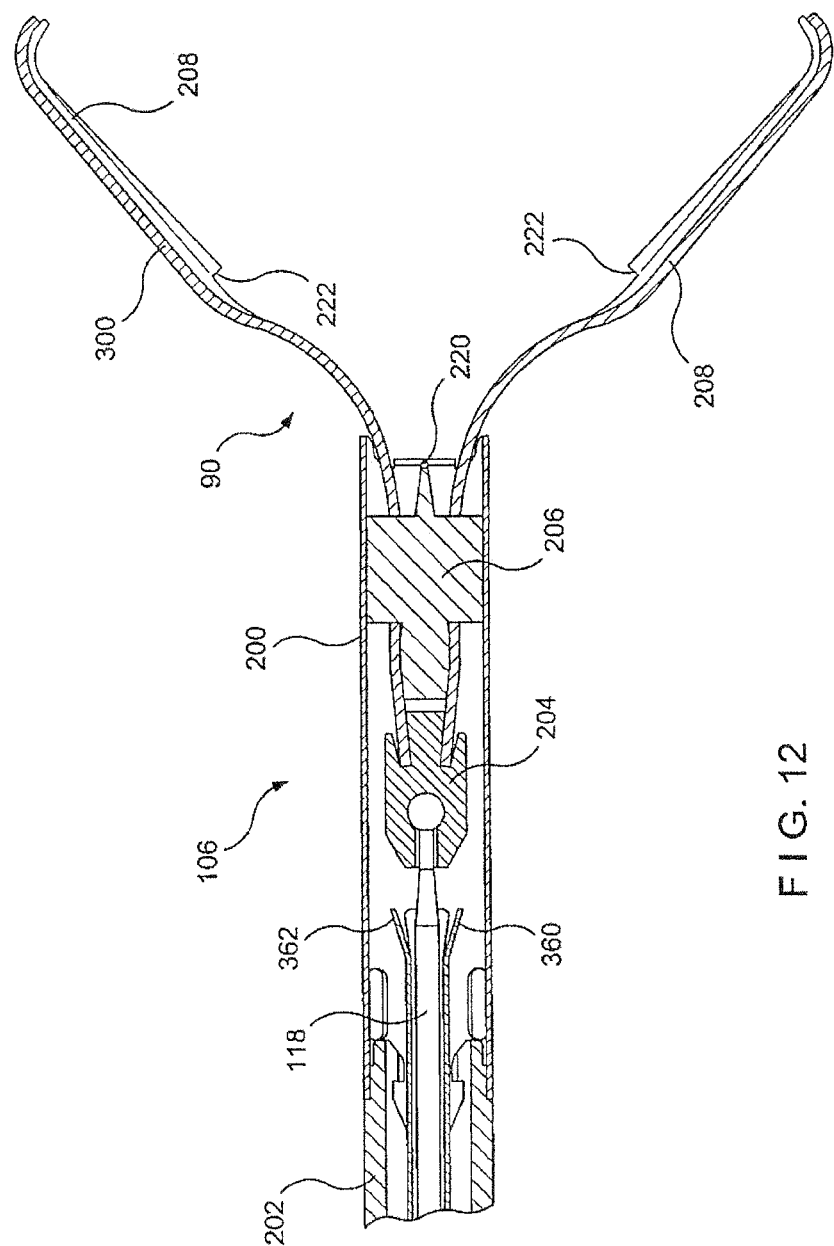
FIG. 12 is a top view of the distal end of a device according to an embodiment of the present invention with the clip arms extended therefrom.
Figure 13:
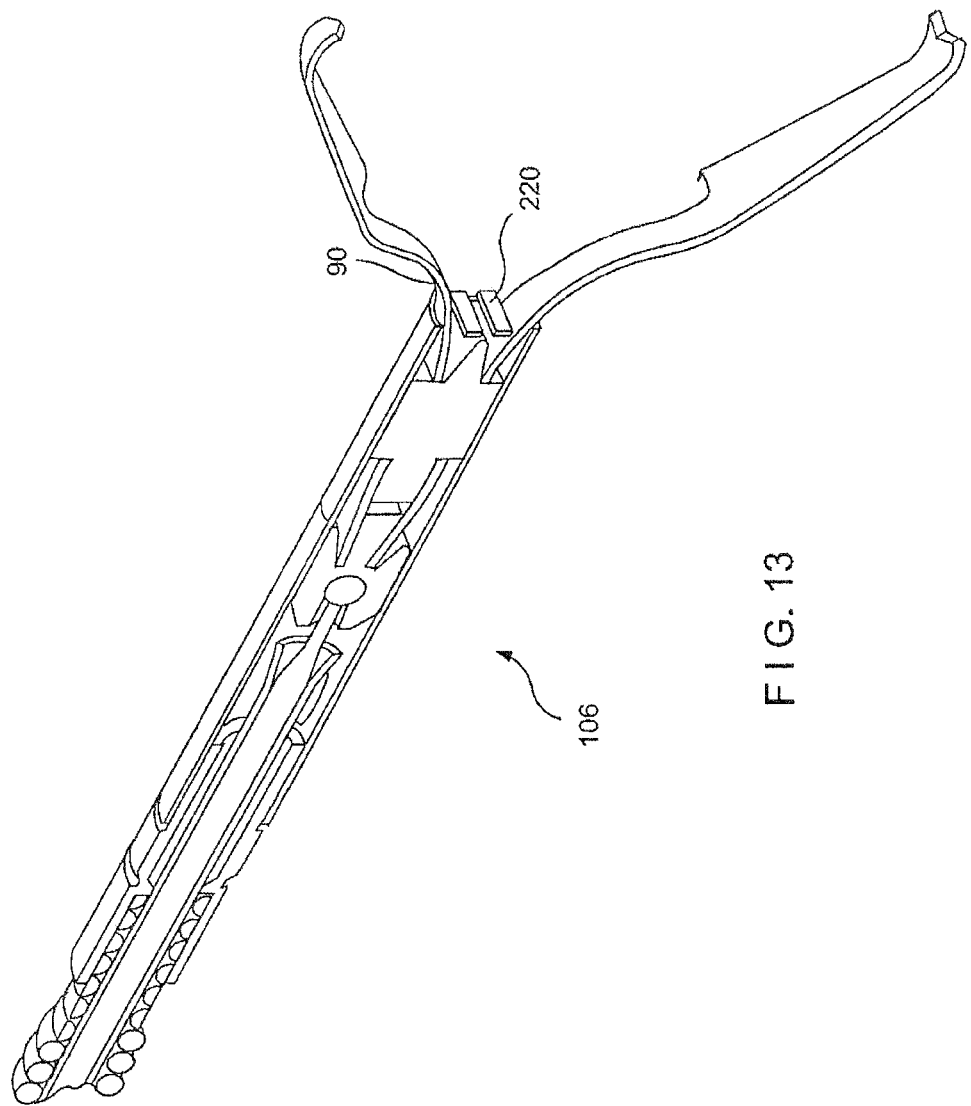
FIG. 13 is a perspective view of the device shown in FIG. 12.
Figure 14:
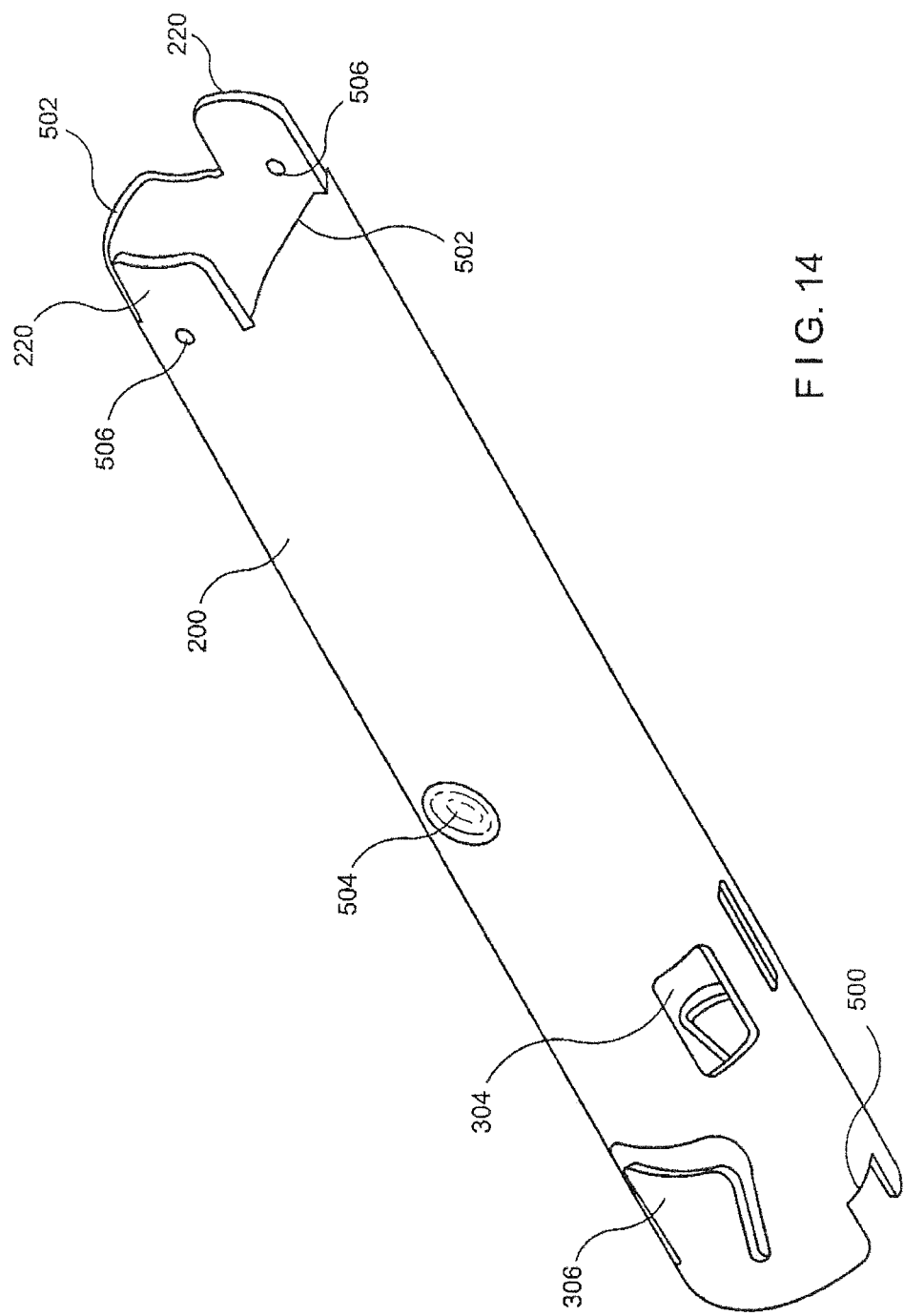
FIG. 14 is a perspective view of a capsule according to an embodiment of the present invention.
Figure 15:
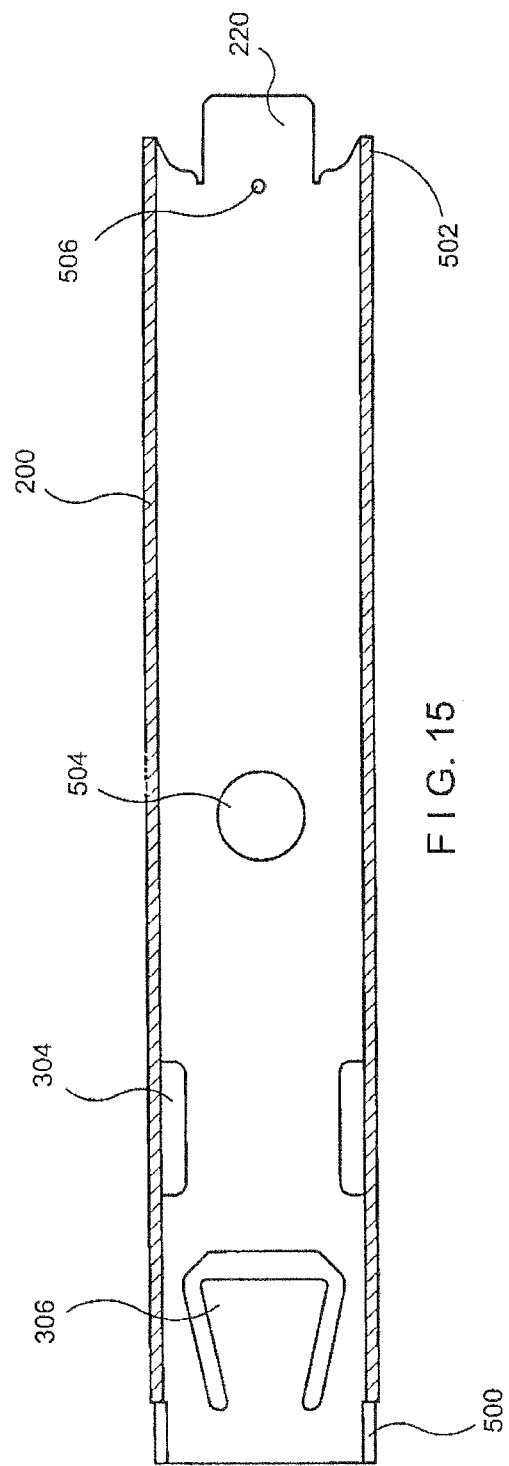
FIG. 15 is a cross sectional side view of the of the capsule shown in FIG. 14.

FIGS. 12 and 13 show a top and a perspective view of one exemplary embodiment of the clip assembly 106 in an open configuration, with the clip arms 208 in a fully open position. The open configuration is obtained when the sliding spool 110 shown in FIG. 1 is moved distally so that the ball 140 of the control wire 118 pushes the assembly containing the yoke 204 and the tension member 206 distally within the capsule 200. As will be described below, the distal ends of the clip arms 208 are biased toward the open position and revert to this position whenever they are not constrained by the capsule 200. In the exemplary embodiment, a maximum opening of the clip arms 208 occurs when the clip arms 208 ride over the folded distal folding tabs 220 which extend from the distal end of the capsule 200, as shown in FIGS. 14 and 15. In this embodiment, the tabs 220 provide a cam surface, and the clip arms 208 act as cam followers, being deflected by the tabs 220, In addition, the folding tabs 220 may also provide a distal stop for the tension member 206, to retain it within the capsule 200. Thus, by moving the sliding spool 110 distally, the user opens the clip arms 208 to prepare to grasp tissue therebetween.

When the sliding spool 110 is moved proximally by the user, the assembly within the capsule 200 also moves proximally and the clip arms 208 are withdrawn within the capsule 200. As the clip arms 208 move proximally within the capsule 200, clip stop shoulders (CSS) 222 contact a distal portion of the capsule 200, for example, the folded tabs 220. This interaction of the CSS 222 with the capsule 200 provides to the user a first tactile feedback in the form of increased resistance to movement of the sliding spool 110. This feedback gives to the operator a positive indication that further movement of the handle control will cause the hemostatic clip 90 to be deployed from the clip assembly 106. The operator may then decide whether the current position of the clip 90 is acceptable or not. If the position is acceptable, the operator can fully deploy the clip 90 by continuing to move the sliding spool 110 with increased proximal pressure to separate the yoke 204 from the tension member 206. If not, the operator can move the sliding spool 110 distally to re-open the clip arms 208 and extend them out of the capsule 200, reposition the clip 90, and repeat the above steps to close the clip 90 at a more appropriate location.

When the user determines that the clipping device 100 is positioned correctly, the proximal pressure on the sliding spool 110 may be increased to continue deployment of the hemostatic clip 90 from the clip assembly 106, FIGS. 16 and 17 show respectively a top and side view of the clipping device 100 in this condition. As the proximal tension on sliding spool 110 is increased, the control cable 118 pulls the yoke 204 proximally, away from the tension member 206. The tension member 206 is firmly attached to the clip arms 208 which are prevented from moving proximally by the interaction of the CSS 222 with the folded tabs 220. If sufficient pulling force is applied to the yoke 204, the male C section 214 of the tension member 206 yields and loses integrity with the female C section 216 of the yoke 204. This can occur because, in the exemplary embodiment, the tension member 206 is formed of a material with a lower yield strength than the material of the yoke 204.

The force required to break the tension member 206 away from the yoke 204 may be tailored to achieve a desired feedback that can be perceived by the user. The minimum force required to break the tension member 206 free of the yoke 204 may be selected so that a tactile feedback is felt by the user, to prevent premature deployment of the hemostatic clip 90 while a maximum force may be selected so that other components of the linkage between the sliding spool 110 and the clip arms 208 do not fail before the male C section 214 and the female C section 216 disconnect from one another. In one exemplary embodiment, the tension force necessary to disconnect the two components may be in the range of approximately 4 lbf to about 12 lbf. This range may vary depending on the size of the device and the specific application. To obtain this force at the interface of the male and female C sections 214, 216 a larger force will be applied by the user at the sliding spool 110, since friction within the device may cause losses along the long flexible shaft.

Figure 18:
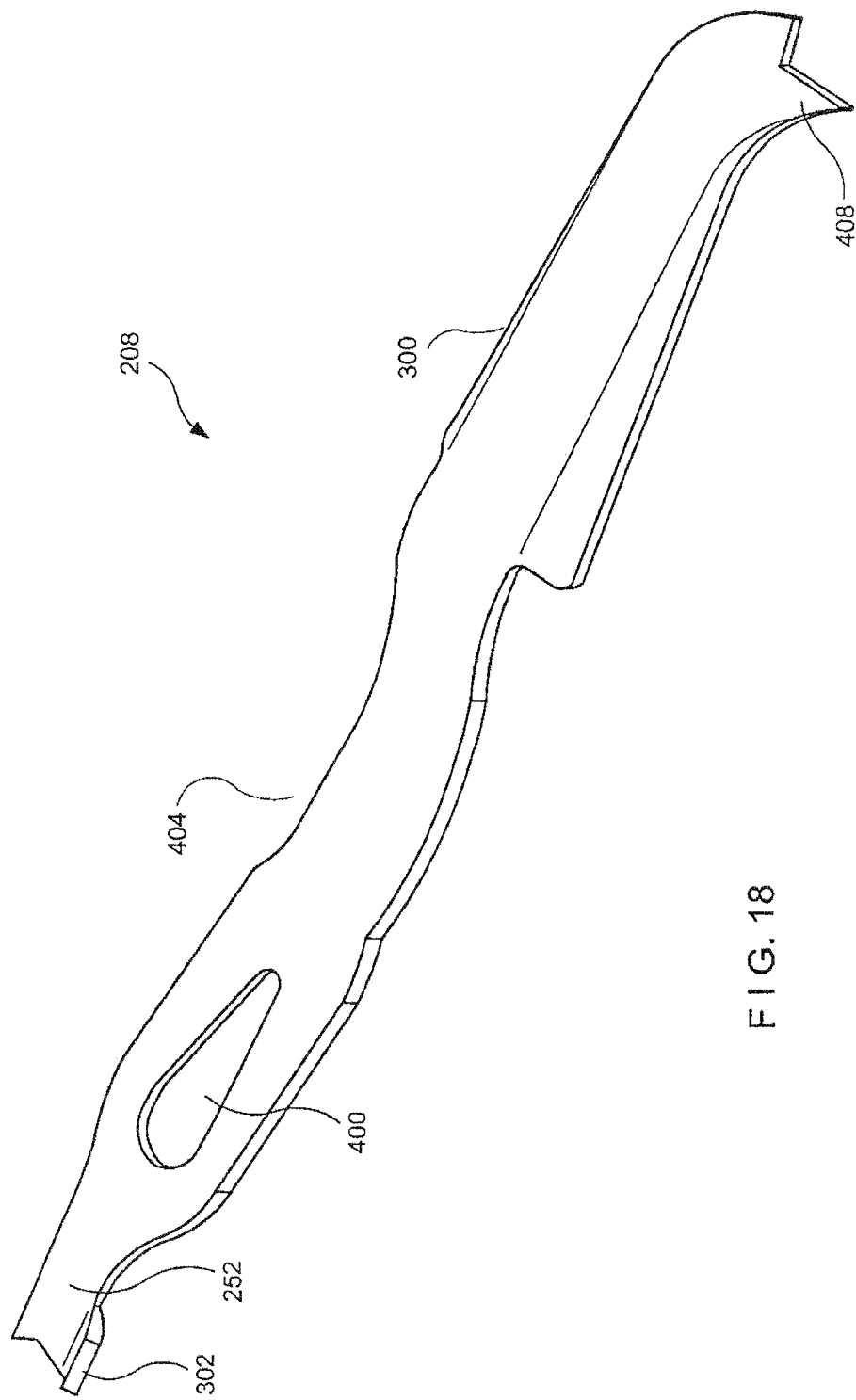
FIG. 18 is a perspective view of a clip arm according to an embodiment of the present invention.

When the male C section 214 of tension member 206 yields, several events take place within the exemplary device 100 nearly simultaneously. More specifically, the yoke 204 is no longer constrained from moving proximally by the CSS 222 abutting the capsule 200. Thus the yoke 204 travels proximally until coming to rest against a distal bushing shoulder 250. The tension member 206 is not affected by this movement since it is no longer connected to the yoke 204. The proximal ends 252 of the clip arms 208 are normally biased away from a center line of the device 100 and are no longer constrained by the yoke overhangs 254. Accordingly, the clip latches 302 are free to engage the latch windows 304 of the capsule 200, thus maintaining the integrity of the capsule-clip arms combination after deployment, Details of one exemplary embodiment of the capsule 200 are shown in FIGS. 14, 15 and details of the clip arms 208 are shown in FIGS. 18, 19 and 20.

Figure 21:
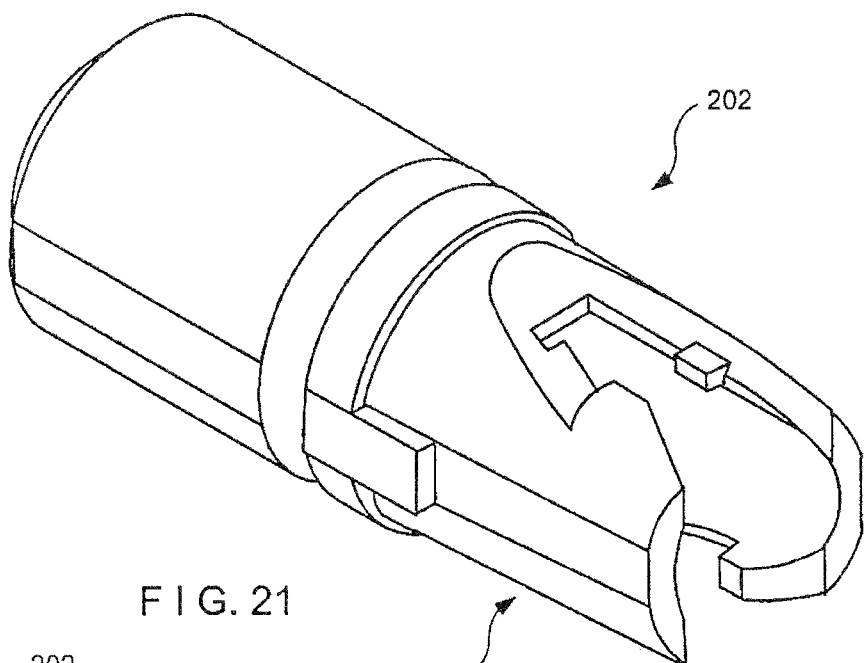
FIG. 21 is a perspective view of a bushing according to an embodiment of the present invention.

As the yoke 204 moves proximally to abut against the bushing 202, the capsule tabs 306 are bent away from the centerline of the capsule 200 by the cam surfaces of the yoke 204. As a result, the capsule tabs 306 no longer engage the corresponding bushing undercuts 350, shown in the side and perspective views of the bushing 202 depicted in FIGS. 21, 22. Since the capsule 200 and the bushing 202 (which is securely connected to shaft section 104) are no longer connected, the clip assembly 106 is prevented from being released from the shaft section 104 only by its connection to the ball 140 of the control wire 118. As will be described in greater detail below, in different exemplary embodiments of the capsule, the capsule tabs 306 may be replaced by different structures.

Figure 22:
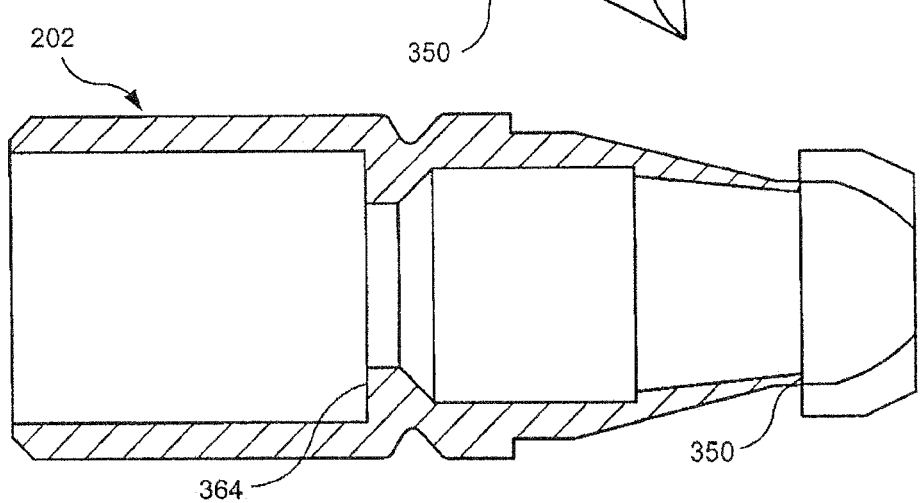
FIG. 22 is a cross sectional side view of the bushing shown in FIG. 21.
Figure 23:
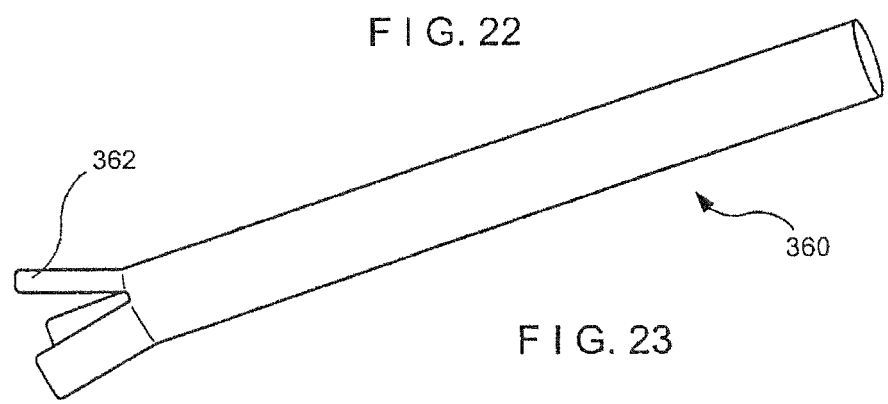
FIG. 23 is a perspective view of a wire stop according to an embodiment of the present invention.

A further result of moving the yoke 204 against the distal bushing shoulder 250 of the bushing 202 is that the distal end of the wire stop 360 (shown in FIGS. 12, 16) is placed near the proximal bushing shoulder 364 (shown in FIG. 22). The flared fingers 362 located at the distal end of the wire stop 360, better shown in FIG. 23, are compressed as they pass through the central ID of the bushing 202, but return to their normally biased open position (shown in FIG. 23) after passing past the proximal bushing shoulder 364. Further distal movement of the sliding spool 110 is thus prevented since that movement would engage the fingers 362 of the wire stop 360 with the proximal bushing shoulder 364. This feature prevents the clip assembly 106 from being pushed away from the bushing 202 before the ball 140 is separated from the control wire 118, as will be described below.

The wire stop 360 comprises a tube with a first slotted and flared end attached to the control wire 118 by conventional means. As shown in FIG. 23, the slots impart flexibility to the device so it can easily pass through the central lumen of the bushing 202, Flared fingers 362 are formed by the slots, and engage the proximal bushing shoulder 364, The wire stop 360 is made of a material that is biocompatible and that has enough resilience so that the fingers 362 re-open after passage through the bushing 202. For example, stainless steel may be used for this application. In different exemplary embodiments that will be described in greater detail below, the wire stop 360 may be omitted from the device.

One feature of the exemplary embodiment of the invention described above is that the user receives both tactile and auditory feedback as the clip assembly 106 is deployed and released. The separation of the tension member 206 from the yoke 204 produces a small clicking noise and a tactile feel that is perceptible while holding the handle assembly 102. The change in axial position of the sliding spool 110 is thus augmented by the changes in resistance to its movement and by the clicking sound and feel through the start and stop of the movement. As a result the user is always aware of the status of the clip assembly 106, and the inadvertent deployment of a hemostatic clip 90 in an incorrect location is made less likely. It will be apparent to those of skill in the art that the order of male and female connectors in the device may be reversed or changed without affecting the operation of the device.

Figure 24:
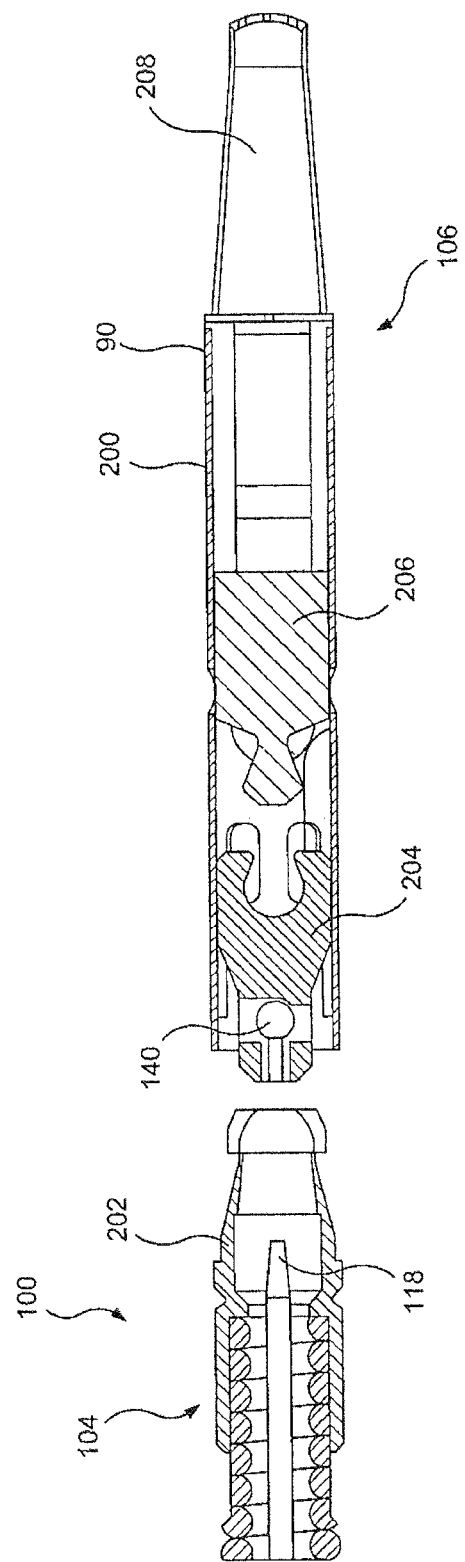
FIG. 24 is a schematic side view of a clip assembly detached from a bushing, according to an embodiment of the present invention.

It may be beneficial for the user to be certain that the clip assembly 106 has been deployed before the rest of the clipping device 100 is removed from the endoscope. Injury to the tissue being treated could result if the clipping device 100 is removed from the operative site when the hemostatic clip 90 is only partially deployed. Accordingly, a large tactile feedback may be incorporated, to augment the auditory and tactile feedback stemming from the separation of the yoke 204 from the tension member 206. FIG. 24 depicts the condition where the clip assembly 106 separates from the rest of the clipping device 100. According to the described embodiment, this second user feedback is obtained by designing the control wire 118 so that it will separate from the end ball 140 when a predetermined tension is applied to it. In other words, the ball 140 of the control wire 118 is mechanically programmed to yield and separate from the body of the control wire 118 when a pre-set tension is applied thereto. The size of the reduced diameter section 142 can be selected so that, when the user continues to move the sliding spool 110 proximally as the programmed yield tension is reached, the ball 140 detaches from the tapered section 144 and provides a large tactile feedback to the operator.

When the ball 140 detaches, the sliding spool 110 bottoms out at the proximal end of the handle 108, such that a full stroke of the handle assembly 102 is reached. The tension required to cause the reduced diameter section 142 to yield and release the ball 140 may vary over a range of values. However, for best results the force should be greater than the tension force required for the male C section member 214 to separate from the yoke 204. If this condition is not satisfied, a situation may occur where the clip assembly 106 is locked in place on the patient's tissue, but cannot be released from the clipping device 100. It will be apparent that this situation should be avoided. In one exemplary embodiment, the tension force required to separate the ball 140 from the body of the control wire 118 is in the range of between about 10 lbf and 20 lbf at the distal end of the control wire 118. As discussed above, losses along the elongated flexible shaft may require the user to apply a force substantially greater than this to the handle body 102.

Once the ball 140 has separated from the rest of the control wire 118, the user can pull the rest of the clipping device 100 from the endoscope. As this is done, the yoke 204 is retained within the capsule 200 by the spring and frictional forces of various features of the capsule 200, such as, for example, the capsule tabs 306. Prior to withdrawing the clipping device 100, the over-sheath 150 may be moved distally by the user over the entire remaining portions of the shaft section 104 to prevent damage to the endoscope as the clipping device 100 is withdrawn therethrough. The sheath stop 156 may also be placed on the shaft section 104 proximally of the over-sheath grip 152 to prevent inadvertent sliding of the over-sheath 150 from the distal end of the device 100.

A more detailed description of several components of the clipping device 100 follows. The clip arms 208 are shown in detail in FIGS. 18, 19 and 20; the tension member 206 is shown in side and top views in FIGS. 25, 26; while top and side views of the yoke 204 are shown respectively in FIGS. 27 and 28, the clip arms 208 may be formed of a biocompatible material such as Nitinol, Titanium or stainless steel. Maximum spring properties may be obtained by using materials such as 400 series stainless or 17-7 PH. As shown, a tear drop keyway 400 is formed in the clip arm 208 to mate with a corresponding tear drop key 402 formed on the tension member 206. This feature maintains the relative positions of these two components and of the yoke 204 substantially constant. The shape of the keyways 400 may be varied. For example, the keyway 400 may be oval or elliptical. Central portions of the clip arms 208 define a spring section 404. When the proximal ends 252 of the clip arms 208 are under the yoke 204 overhangs 254, the clip arms 208 are allowed to pivot over the tension member 206, which in turn biases the distal ends 252 towards the open configuration when no longer restrained by the capsule 200. As a result, the proximal end 252 of each clip arm 208 springs upward and engages the latch windows 304 in the capsule 200.

The clip arms 208 also comprise a radius section 300 that adds strength to the clip and reduces system friction. The radius of the radius section 300 approximately matches the inner diameter of the capsule 200 and has a smooth profile to avoid scratching the inner surface of the capsule 200. A pre-load angle α is defined between the radius section 300 and the spring section 404. The pre-load angle α determines how much interference (pre-load) exists between the two opposing clip arms 208 at their distal ends when closed. The greater the pre-load angle α, the greater the engaging force that is applied by the clip arms 208. However, this condition also causes the greatest system friction when the hemostatic clip 90 is closed. The clip arms 208 also comprise interlocking teeth 408 disposed at their distal ends. In the exemplary embodiment, the teeth 408 are identical so that the arms may be interchangeable and will mesh smoothly with the set facing them. The teeth 408 are disposed at a nose angle β which may be between approximately 90 and 135 degrees, but in other applications may be greater or lesser than the described range.

One exemplary embodiment of the capsule 200 is shown in detail in FIGS. 14 and 15. The device comprises alignment keyways 500 that are designed to mate with corresponding features on the bushing 202 to rotationally align the two components. In this exemplary embodiment, the capsule tabs 306 may be bent towards the centerline of the capsule 200 to engage the bushing undercuts 350. The engagement maintains the integrity between the capsule assembly 200 and the rest of the clipping device 100 until the yoke 204 is pulled into the distal bushing shoulder, the capsule overhangs 502 provide added clamping strength to the deployed clip arms 208. This is achieved by reducing the length of the portion of each clip arm 208 that is not supported by a portion of the capsule 200. This feature does not affect the amount of tissue that may be captured by the clip arms 208 since the capsule overhangs 502 extend on a plane substantially parallel to the plane of the clip arms 208.

Additional features of the capsule 200 include an assembly aid port which may be used to assist in aligning the components of the clip assembly 106. Bending aids 506 facilitate a smooth bend when the distal folding tabs 220 are bent inward, as described above. The bending aids 506, as shown, are holes aligned with the folding line of the tabs 220, but may also include a crease, a linear indentation, or other type of stress concentrator. The capsule 200 may be formed from any of a variety of biocompatible materials. For example, stainless steel, Titanium or Nitinol or any combination thereof may be used. High strength polymers like PEEK™ or Ultem™ may also be used to form the capsule 200, with a heat set treatment being used to adjust positionable elements.

A different exemplary embodiment of the present invention is shown in FIGS. 30-33. In this embodiment, several features of the clip capsule and of the control wire actuation mechanism are modified to further facilitate the release of the clips from the delivery mechanism. As indicated above, it is important to ensure that the clip completely separates from the control wire after deployment to prevent a situation where the clip is clamped to the patient's tissue, but cannot be released from the deployment mechanism. Accordingly, the exemplary embodiment shown in FIGS. 30-33 incorporates design features which reduce mechanical side loads between the clip capsule and the bushing, and facilitate a smoother and more certain disengagement of the clip.

More specifically, the present exemplary embodiment incorporates an interface portion 816 of the clip capsule 804 that is axially shorter than this portion in the above-described embodiments. For example, the interface portion 816 may up to 60% shorter in this embodiment than in the above-described embodiments. The interface portion 816 is adapted to releasably connect with the bushing 806 to temporarily provide structural strength to the assembly. The exemplary embodiment also incorporates a different distal end of the control wire 810, which can be used to help separate the clip 802 and capsule 804 from the bushing 806.

FIGS. 34-37 show in greater detail the capsule 804 according to the exemplary embodiment also shown in FIGS. 30-33. FIGS. 38 and 39 show the corresponding bushing 806, which is adapted to cooperate with the capsule 804 to provide a smoother separation of the clip 802 from the delivery mechanism. Several features of the present exemplary capsule 804 are similar to features of the embodiments described above and carry out the same functions. For example, the key ways 820 are designed to cooperate with features 822 of the bushing 806 to rotationally align the two components. The latch windows 824 also perform the same function as described above with respect to other embodiments and cooperate with proximal ends of the clips 802.

One feature of the present embodiment is a shortened interface portion 816 which comprises a different releasable locking mechanism to connect the capsule 804 to the bushing 806. In this embodiment, an "A" frame tab 830 is designed to cooperate with bushing hooks 832 to temporarily maintain the capsule 804 and the bushing 806 attached to one another. FIGS. 40-43 show additional views of the capsule 804 while it is connected to the bushing 806. During assembly of the delivery device, the two components are attached by moving the capsule 804 over the bushing 806 and then bending the "A" frame tabs 830 into the bushing hooks 832. The inside distal edge 834 of each "A" frame tab 830 is pushed down when joining the two components and locks behind the bushing hooks 832.

As a clip 802 is deployed to clamp tissue and is then released from the deployment device 800, the "A" frame tabs 830 disengage from the hooks 832 of the bushing 806 after the tension member 814 has been broken and the cam surfaces of the yoke engage the "A" frame tabs 830 as described above. The release sequence is accomplished through movement of the internal components within the capsule 804 in response to movement of the sliding spool 110 and the handle 108 (FIG. 2), as described above with reference to the previous exemplary embodiments of the device.

A second feature included in this embodiment of the clip delivery device 800 comprises a control wire 810 and a hypo tube 900, as shown in FIGS. 30-33. In the present exemplary embodiment, no wire stop is included and the control wire 810 may be used to push the clip 802 away from the clip delivery device 800 after deployment of the clip 802 therefrom. This additional function of the control wire 810 may be utilized after the control wire ball 902 has separated from the control wire 810, for example by programmed failure of the reduced diameter section 904. Using the control wire 810 to push the deployed clip 802 provides additional assurance that, when the clip 802 is clamped to the patient's tissue. It will be completely released from the clip delivery device 800.

According to the exemplary embodiment shown herein, after failure of the tension member 814 and before the control wire 810 is severed, if a user pushes the control wire 810 distally in an attempt to re-open the clip 802, the clip 802 will remain coupled to the tissue while bound to the control wire 810. At this point, due to the shorter longitudinal length of the clip capsule 804, the yoke 812 may be drawn out of the proximal end of the capsule 804 by proximal movement of the control wire 810. The bushing 806 may then be moved distally as the yoke 812 is drawn proximally to draw the proximal tapered end of the yoke 812 into the distal opening in the bushing 806. The proximal tapered end of the yoke 812 allows the yoke 812 to be realigned with the bushing 806 as the yoke may have rotated about the control wire ball 902. After the yoke 812 has been re-aligned with the bushing 806, the control wire 810 may be drawn further proximally to separate the control wire ball 902 from the proximal portion of the control wire 810 to completely release the clip 802.

One mode of operation of the exemplary embodiment of the clip release device 800 is described with reference to FIGS. 30-33, and also referring back to FIGS. 1 and 2. After the reduced diameter section 904 has yielded and the control wire 810 has been separated from the control wire ball 902, the sliding spool 110 is advanced distally by the user relative to the handle 108 so that the distal (separated) end of the control wire 810 pushes the clip 802 distally away from the clip delivery device 800, providing a further assurance that the clip 802 has completely separated from the delivery device 800. The user may then safely remove the delivery device 800.

After the reduced diameter section 904 has yielded, the distal end of the control wire 810 may be jagged or sharp. To limit the possibility of injury from the sharp end of the control wire 810, a protective shroud, e.g., the hypo tube 900, is placed around the distal portion of the control wire 810. For example, the hypo tube 900 may be crimped onto the control wire 810, causing both to move together longitudinally in and out of the catheter. It will be apparent to those of skill in the art that other methods of attaching the hypo tube 900 to the control wire 810 may be used without departing from the scope of the invention. The hypo tube 900 placed around the sharp end of control wire 810 acts as a blunt surface to minimize trauma to tissue against which the control wire 810 may be pushed. In addition, the hypo tube 90 stiffens the reduced diameter section of the control wire 810 to aid the reduced diameter section in resisting buckling when subjected to compression as the control wire 810 is moved distally.

In the present exemplary embodiment, the control wire 810 is free to move longitudinally along the clip delivery device 800. Accordingly, various internal passages of the delivery device 800 are sized to prevent interference with the movement of the control wire 810. For example, an inner diameter of the bushing shoulders 906 may be such that the hypo tube 900 can pass therethrough without catching the lip of the bushing shoulders 906. This feature further facilitates longitudinal movement of the control wire 810 and its use to push deployed clips 802 longitudinally away from the deployment device 800.

The exemplary embodiment of the clip delivery device 800 described above thus promotes a more positive and smooth separation of the clip 802 after it has clamped on the target tissue and before the delivery device 800 is withdrawn from the patient's body. A clip capsule 804 having a shorter longitudinal length and "A" frame locking tabs may promote a smoother separation of the capsule 804 from the bushing 806, by reducing the side loads that may exist during deployment and using the control wire 810 to push the clip 802 out of delivery device after clamping to the target tissue provides a further assurance of positive release.

Figure 26:
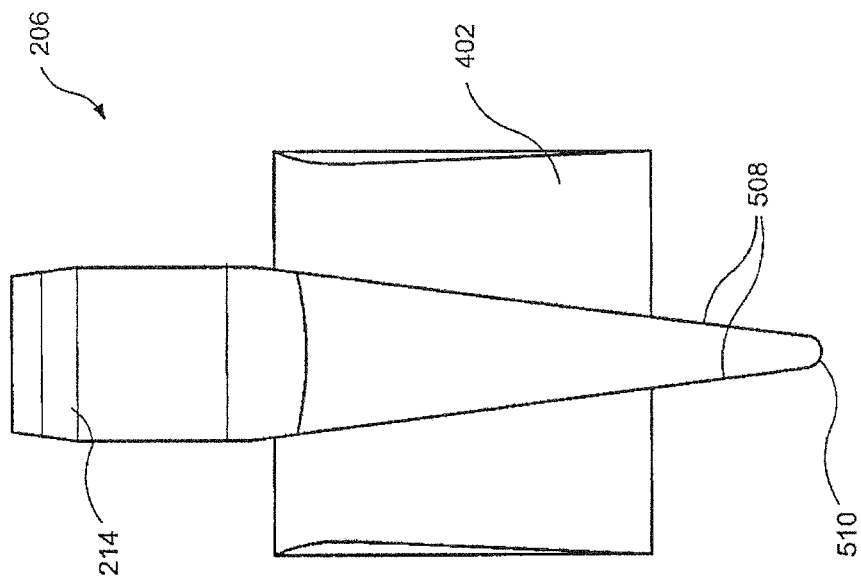
FIG. 26 is a top view of the tension member shown in FIG. 25.
Figure 25:
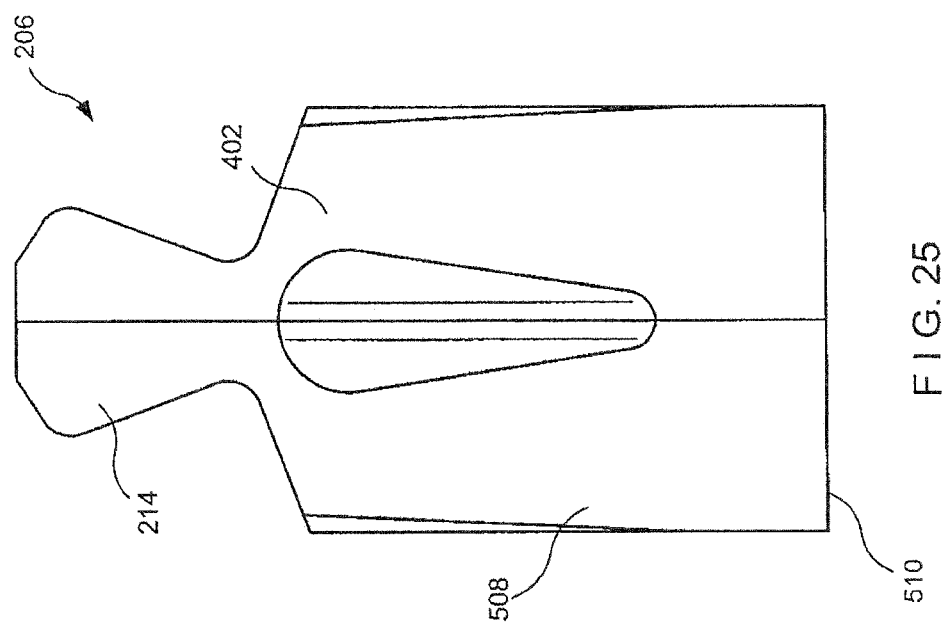
FIG. 25 is a side view of a tension member according to an embodiment of the present invention.

FIGS. 25 and 26 depict additional details of the tension member 206. As shown, tear drop keys 402 are designed to engage the tear drop keyways 400 of the clip arms 208, as described above. Clip follower planes 508 are shaped to form a fulcrum which allows the clip arms 208 to rock between the open and closed configurations. The tension member 206 comprises a distal stop face 510 which abuts the distal folding tabs 220 of the capsule 200 to stop the distal motion of the capsule assembly 106. In general, all surfaces and edges of the tension member 206 that are in contact with the inner surfaces of the capsule 200 preferably have a radius substantially similar to an inner radius of the capsule 200 to provide a sliding fit therein. The tension member 206 may be formed of a biocompatible polymer, monomer or thermoset. The type of mechanism selected to release the tension member 206 from the yoke 204 may determine the type of material used since a release due to fracture of the male C section 214 requires a relatively brittle material while release due to yielding without fracture calls for a softer material.

Figure 27:
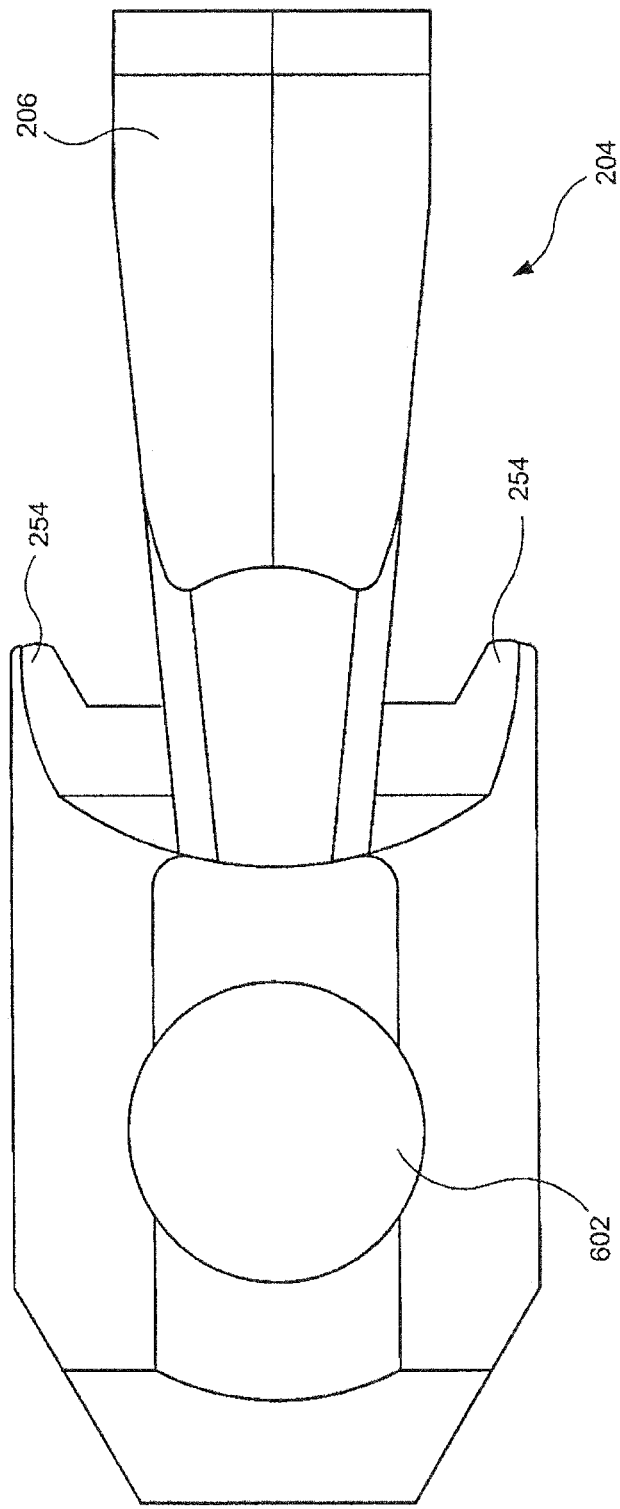
FIG. 27 is a top view of a yoke according to an embodiment of the present invention.
Figure 28:
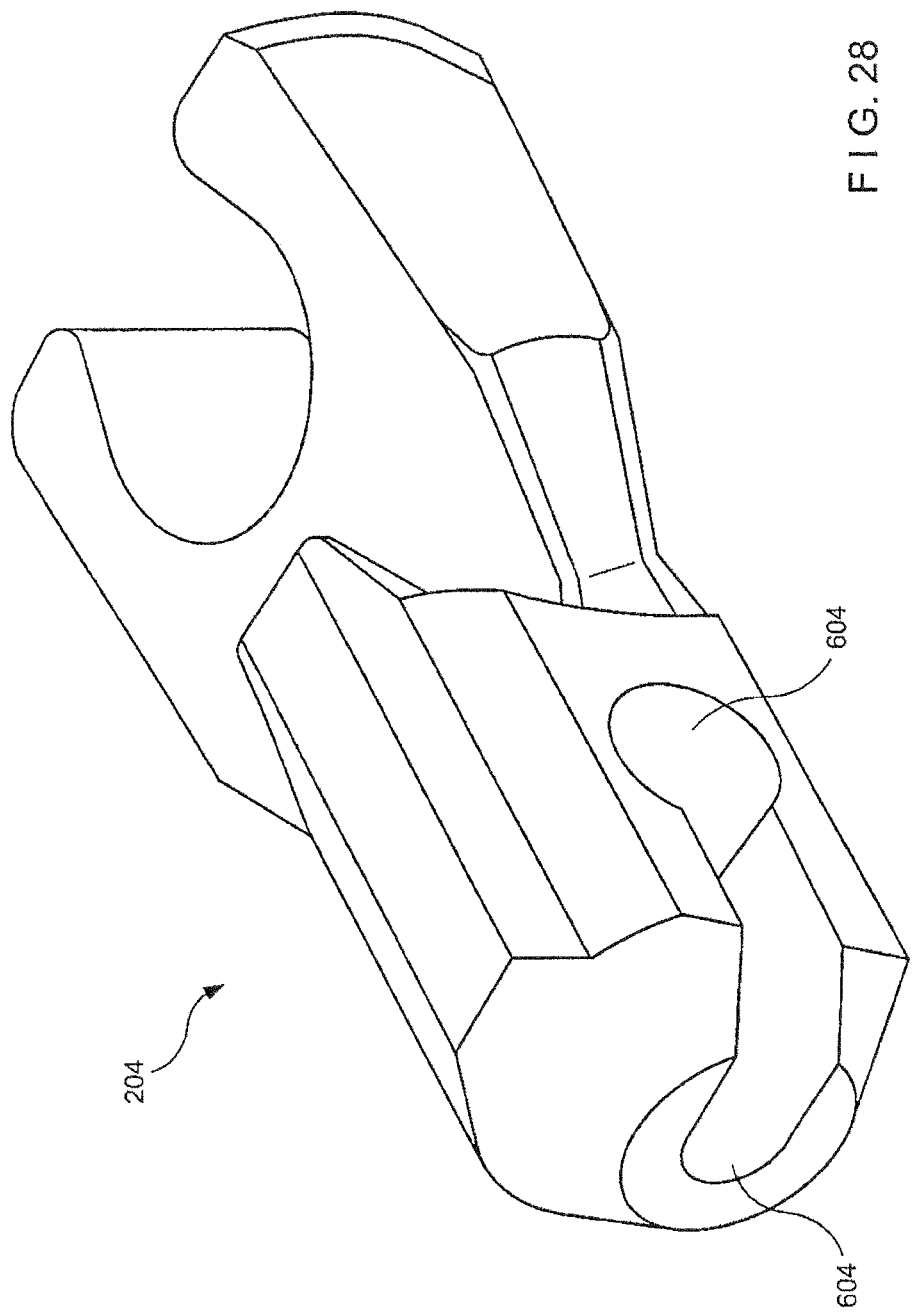
FIG. 28 is a perspective view of the yoke shown in FIG. 27.
Figure 29:
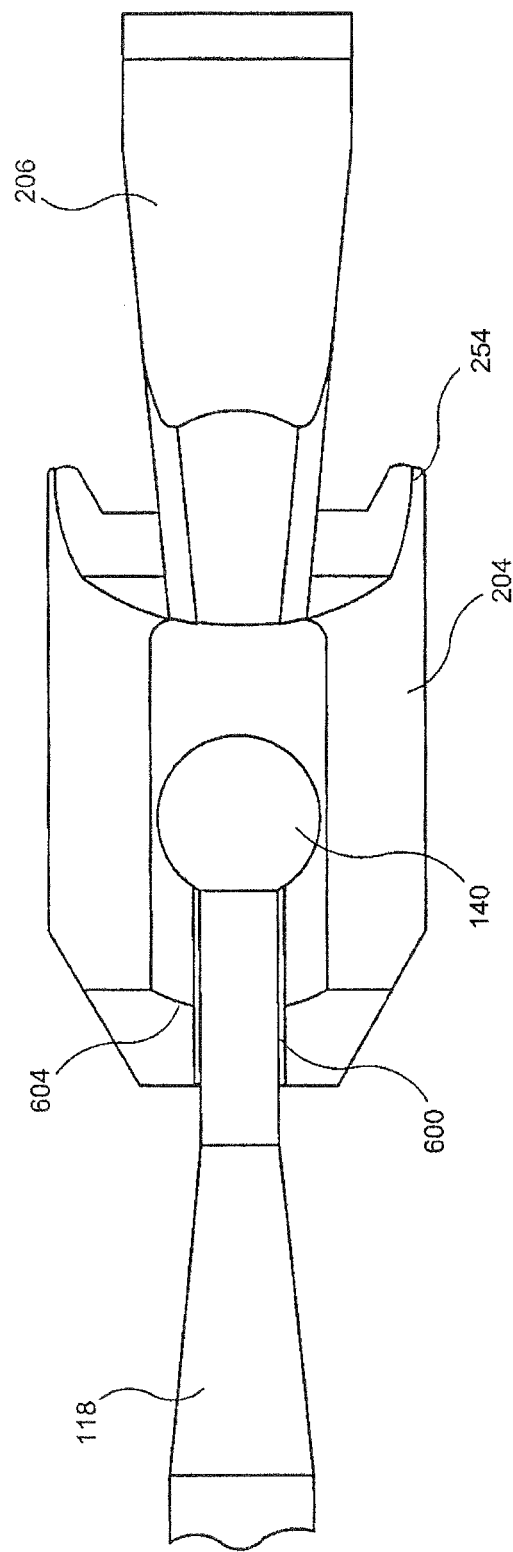
FIG. 29 is a top view of a yoke with a control wire according to an embodiment of the present invention.
Figure 30:
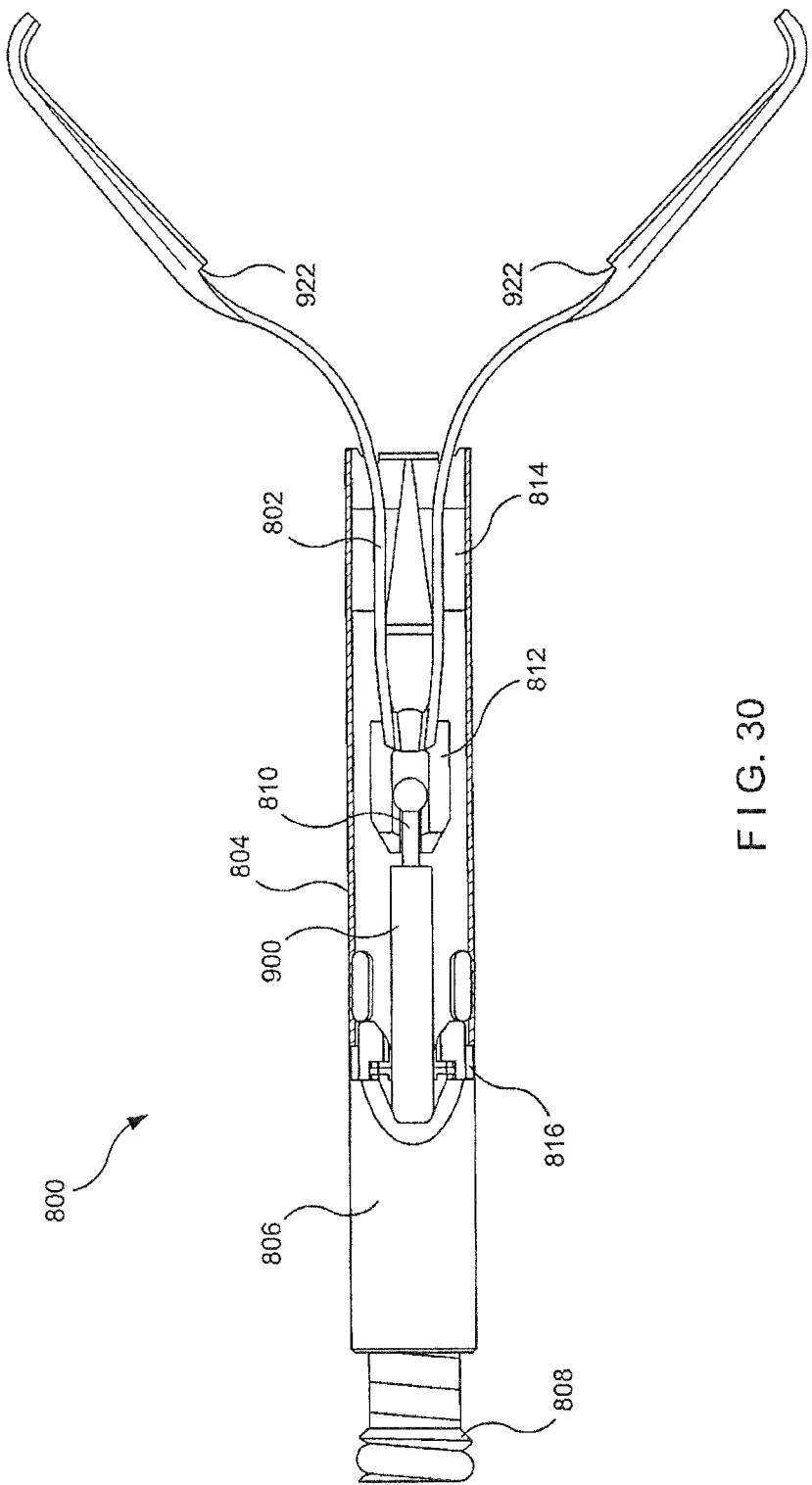
FIG. 30 is a partially cross-sectional, side view of a different embodiment of the present invention.
Figure 31:
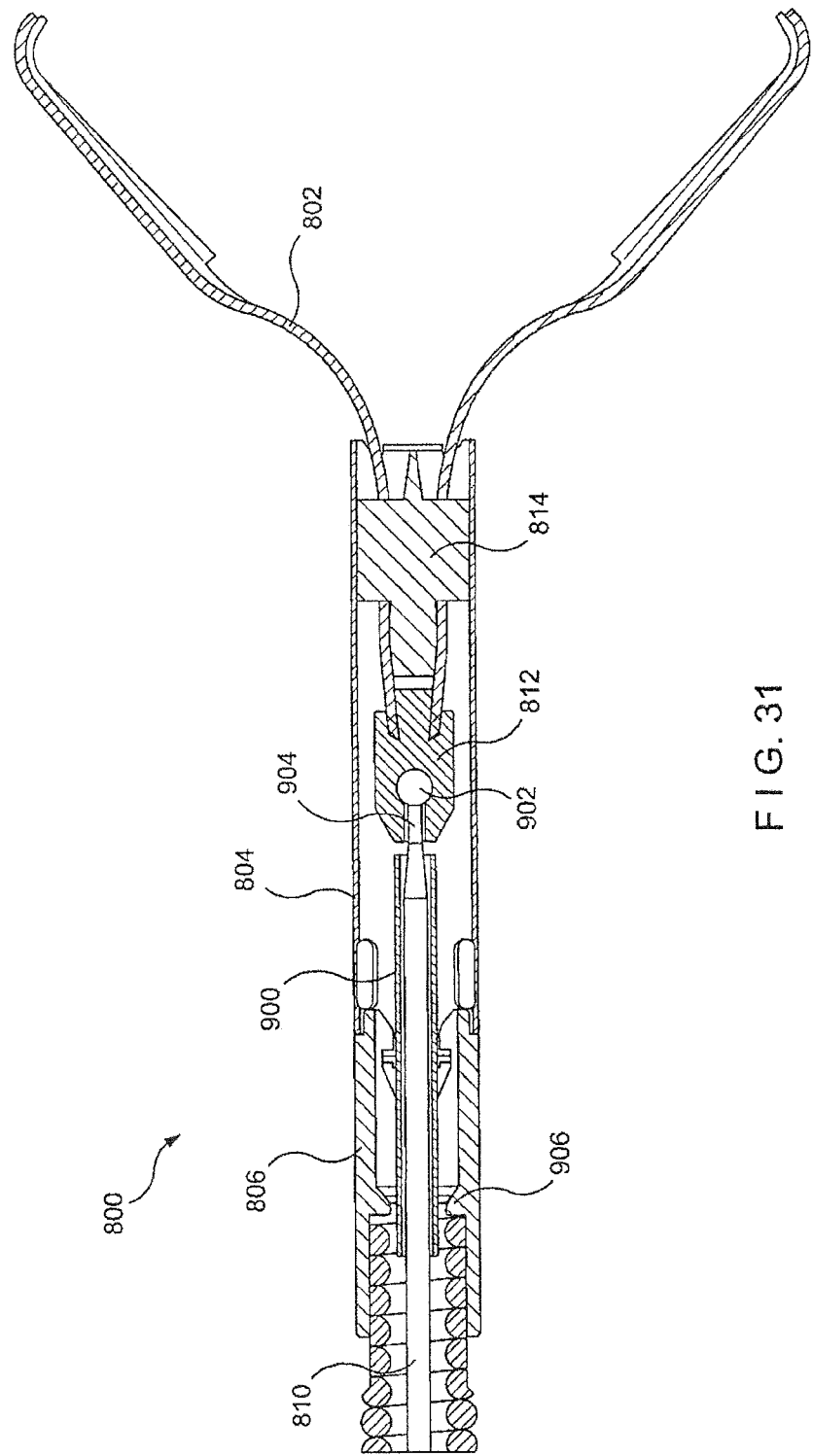
FIG. 31 is a cross sectional view of the embodiment shown in FIG. 30.
Figure 32:
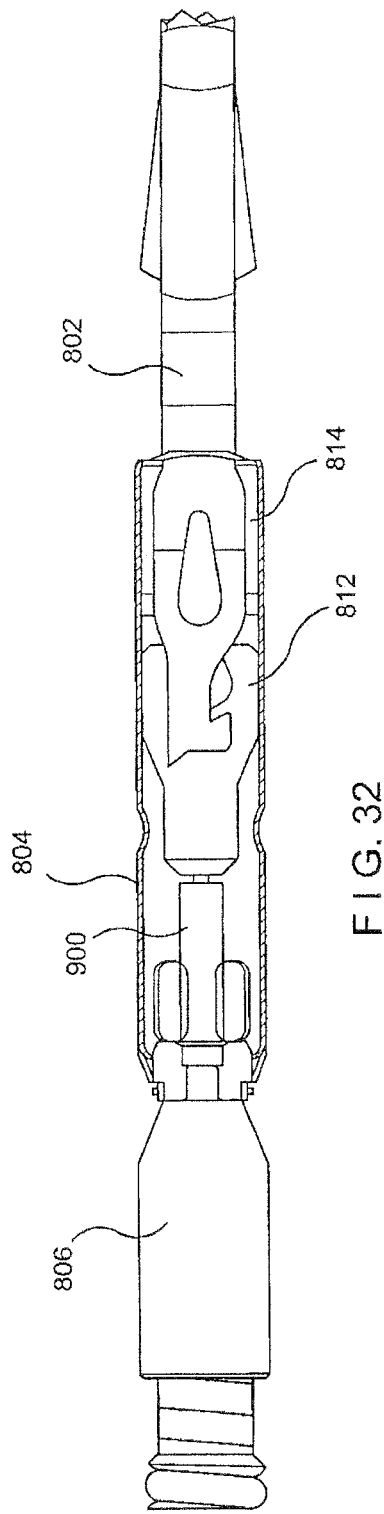
FIG. 32 is a partially cross-sectional, top view of the embodiment shown in FIG. 30.
Figure 33:
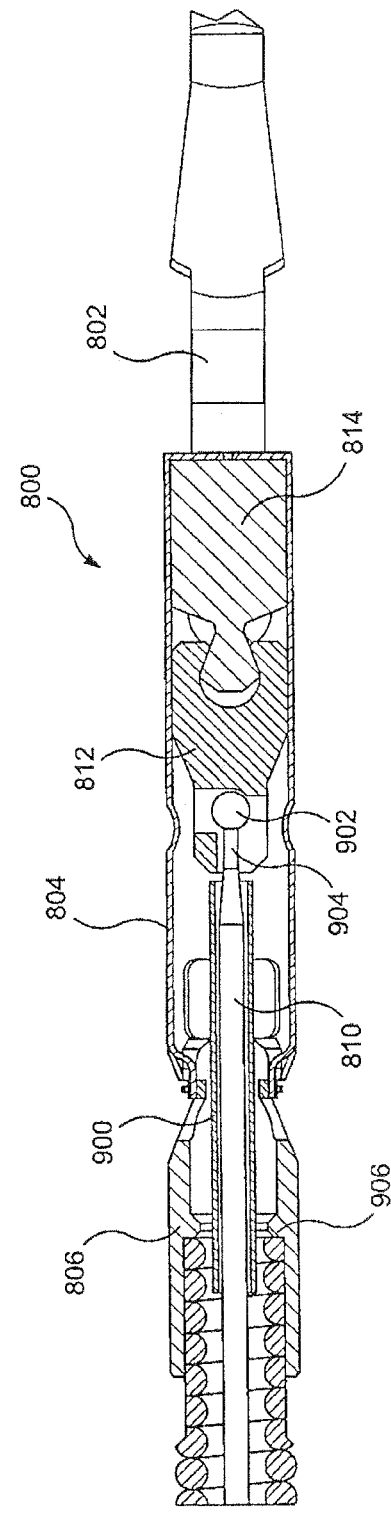
FIG. 33 is a cross-sectional view of the embodiment shown in FIG. 32.

Additional details of the yoke 204 are shown in FIGS. 27-29. When the control wire 118 is seated in the yoke 204, it is desirable to ensure that it cannot inadvertently be removed from the control wire slot 600. Accordingly, in the present embodiment the ball cavity 602 has a diameter sufficiently large to allow the ball 140 to pass therethrough while the wire cavity 604 is large enough to allow the control wire 118 to pass therethrough, but not large enough to allow the ball 140 pass therethrough. To assemble the control wire 118 with the yoke 204 according to the exemplary embodiment, the proximal end of wire 140 is inserted into the ball cavity 602 until the ball bottoms out, and then the control wire 118 is rotated until it is seated in the control wire cavity 604, thus constraining further movement of the ball 140. According to the present embodiment, the yoke 204 may be made of a biocompatible metal such as stainless steel or a high strength polymer such as Ultem™.

According to embodiments of the present invention, the clipping device 100 may be scaled to fit the requirements of different surgical procedures. In one exemplary embodiment, the clipping device 100 may be sized to fit through an endoscope having a working channel diameter of approximately 0.110 inches. The exemplary bushing may have a length of about 0.22 inches and an OD of approximately 0.085 inches. The capsule may have a length of about 0.5 inches, an OD of about 0.085 inches, and a wall thickness of about 0.003 inches. When assembled, the rigid length of the capsule 200 and the bushing 202 is approximately 0.625 inches. This length is important because if it is too great, the assembly will not pass through the bends of the flexible endoscope. In the exemplary clipping device, the outer sheath may have an ID of approximately 0.088 inches and an OD of about 0.102 inches. The overall length of the clipping device may be approximately 160 inches, while the tissue grasping portion of the clip arms 208 may be approximately 0.4 inches long.

Several aspects of the present invention are described below. In one aspect, the present invention is directed to an apparatus for deployment of a hemostatic clip comprising a handle assembly, a shaft connected to a distal portion of the handle assembly, a clip assembly releasably coupled to a distal portion of the shaft, the clip assembly including clip arms and a capsule cooperating with the clip arms to provide a first user feedback indicating a decision configuration of the clip assembly, and a control wire including a ball connector, the control wire extending from the handle assembly and coupled to the clip assembly by the ball connector to maintain the clip assembly coupled to the shaft, wherein the ball connector is detachable from the clip assembly to provide a second user feedback indicating separation of the clip assembly from the shaft.

The apparatus further includes an over sheath movable between a first position covering the shaft and the clip assembly and a second position uncovering the clip assembly. The over sheath has an over sheath stop engageable on the shaft to prevent movement of the over sheath to the second position.

The clip arms further comprise stop shoulders engaging a distal end of the capsule to provide the first user feedback during proximal movement of the control wire. The decision configuration indicates a position of the control wire beyond which further proximal movement of the control wire precludes return of the clip arms to an open configuration by a reversed movement of the control wire.

The capsule of the apparatus for deployment of a hemostatic clip further comprises a yoke including a ball cavity and being slidable within the capsule, the yoke receiving the ball connector in the ball cavity, and a tension member releasably connected to the yoke, the tension member being connected to the clip arms and biasing the clip arms toward an open configuration, wherein the tension member releases from the yoke when the control wire is moved proximally beyond the position at which the first user feedback is provided. The tension member and the yoke are releasably connected to one another by a male C section member and a female C section member. Separation of the yoke and tension member occurs by one of fracture and deformation of the male C section member.

In the apparatus for deployment of a hemostatic clip, separation of the yoke and tension member occurs when a tension on the control wire tension is at least a predetermined separation tension. For example, the separation tension is at least approximately 4 lbf, or alternatively may be less than approximately 12 lbf. The separation of the yoke and tension member locks the clip arms in a closed configuration by sliding the tension member and the clip arms proximally within the capsule. Separation of the yoke and tension member also allows proximal movement of the yoke to release the capsule from a bushing of the shaft. Distal movement of the control wire, before separation of the yoke from the tension member, slides the clip arms distally out of the capsule into an open configuration.

In the apparatus for deployment of a hemostatic clip, the first feedback includes a tactile and aural feedback. The control wire further comprises a reduced diameter section adjacent to the ball connector, the reduced diameter section yielding when a tension in the control wire reaches a predetermined yield tension. The yield tension is greater than the separation tension, and may be between approximately 10 lbf and 20 lbf.

In another aspect, the invention is directed to a clip deployment apparatus insertable to locations within a body through an endoscope. The apparatus includes an elongated member extending from a proximal end to a distal end, a control wire extending from the proximal end of the elongated member to the distal end thereof, a bushing coupled to the distal end of the elongated member, and a capsule releasably connected to the bushing. The apparatus further includes clip arms slidable within the capsule between a distal open configuration and a proximal closed configuration, a tension member slidable with the clip arms, the tension member biasing the clip arms toward the open configuration, and a yoke slidable within the capsule, a first end of the yoke being releasably connected to the tension member and a second end of the yoke being connected to the control wire, wherein distal movement of the control wire slides the clip arms into the open configuration, and proximal movement of the control wire slides the clip arms into the closed configuration.

In the apparatus described above each of the clip arms comprises a radius section and wherein the capsule comprises a plurality of overhangs cooperating with the radius sections to retain the clip arms in the closed configuration when the clip arms are moved proximally within the capsule. Each of the clip arms also comprises stop shoulders and wherein the capsule comprises a plurality of distal folding tabs cooperating with the stop shoulders to provide a first user feedback indicative of proximal movement of the clip arms through a selected position in the capsule. The first user feedback includes an aural component and a tactile component.

The proximal movement of the control wire beyond a point at which the clip arms are in the selected position results in separation of the yoke from the tension member. The separation of the yoke from the tension member precludes returning the clip arms to the open configuration and allows further proximal movement of the yoke to release the capsule from the bushing.

The apparatus described further comprises a ball and socket connection between the yoke and the control wire. That ball and socket connection includes a ball detachably coupled to a body of the control wire when a tension on the control wire is at least a predetermined separation tension, the ball providing a second user feedback when separated from the body of the control wire.

In yet another aspect, the invention is directed to a method for hemostatic clipping comprising inserting a shaft of a clipping device through a working lumen of an endoscope, wherein the shaft extends to a distal clipping assembly of the clipping device including a plurality of clip arms and wherein a control wire extends through the shaft from the clipping assembly to a handle coupled to a proximal end of the shaft. The method also comprises manipulating the handle assembly to move a control wire within the shaft to move the clip arms between an open and a closed configuration, generating a first user feedback indicating a decision configuration of the apparatus, and generating a second user feedback indicating separation of the clipping assembly from the shaft.

The method according to the present invention further comprises covering the shaft and the clipping assembly with an outer sheath and sliding the outer sheath proximally to uncover the clipping assembly. The clipping assembly further comprises a capsule slidably containing a yoke and a tension member biasing the clip arms toward the open configuration, the yoke being coupled to the control wire and being detachably coupled to the tension member.

The step of giving the first user feedback comprises providing a resistance force ending proximal movement of the clip arms and increasing a resistance to a corresponding movement of the handle assembly. Also included is separating the yoke from the tension member when a tension applied to the control wire after generation of the first user feedback is at least a first pre-selected tension. The second user feedback is generated when a reduced diameter portion of the control wire yields when a tension applied to the control wire is at least a second pre-selected tension, which may be greater than the first pre-selected tension.

The present invention has been described with reference to specific exemplary embodiments. Those skilled in the art will understand that changes may be made in details, particularly in matters of shape, size, material and arrangement of parts without departing from the teaching of the invention. Accordingly, various modifications and changes may be made to the embodiments without departing from the broadest scope of the invention. The specifications and drawings are, therefore, to be regarded in an illustrative rather than a restrictive sense.

The present invention has been described with reference to specific exemplary embodiments. Those skilled in the art will understand that changes may be made in details, particularly in matters of shape, size, material and arrangement of parts without departing from the teaching of the invention. For example, different shapes of the yoke, the tension member and the bushing may be used, and different attachments of the clip arms and control wire may be employed. Accordingly, various modifications and changes may be made to the embodiments without departing from the broadest scope of the invention as set forth in the claims that follow. The specifications and drawings are, therefore, to be regarded in an illustrative rather than a restrictive sense.

The invention claimed is:

1. An apparatus for applying clips to tissue, comprising:
a flexible sheath extending from a proximal end configured to extend into a living body to a target portion of tissue to be clipped;
a capsule comprising a proximal end and a distal end;
a clip assembly provided in the capsule and configured to be operably movable between a closed configuration in which distal ends of first and second arms of the clip assembly are drawn toward one another and an expanded configuration in which the distal ends of the first and second arms are separated from one another to receive target tissue therebetween; and
a control member a distal end of which is releasably coupled to the clip assembly via a yoke to transmit to the clip assembly forces applied to the control member to move the clip assembly between the closed and expanded configurations, wherein the yoke engages proximal ends of the first and second clip arms, the yoke including first and second yoke arms extending distally from the control member on opposite sides of the clip assembly, a connecting member extending between the first and second yoke arms coupling the yoke to the clip assembly, the first and second yoke arms being configured to be separated from the connecting member when subjected to a predetermined force by the control member to uncouple the control member from the clip assembly.

2. The apparatus of claim 1, further comprising a bushing coupled between the flexible sheath and the capsule, the bushing being releasably coupled to the proximal end of the capsule and being fixed to the distal end of the flexible sheath.

3. The apparatus of claim 2, wherein the flexible sheath is formed as a wire coil and the bushing is a substantially cylindrical member extending distally therefrom with a distal portion of the bushing being received within the capsule.

4. The apparatus of claim 1, wherein the control member includes an increased diameter portion at a distal end thereof, the increased diameter portion being coupled to the yoke.

5. The apparatus of claim 1, wherein the first and second yoke arms extend distally past the proximal ends of the first and second arms of the clip assembly.

6. The apparatus of claim 5, wherein the distal ends of each of the first and second yoke arms include a portion that hooks around a portion of the connecting member to connect the connecting member to the control member.

7. The apparatus of claim 4, wherein the increased diameter portion at the distal end of the control member is immovably fixed to a portion of the control member.

8. The apparatus of claim 1, wherein the proximal end of the first arm of the clip assembly includes a locking feature positioned to mechanically lock with a corresponding locking feature of the capsule when the yoke is separated from the connecting element and the yoke is disengaged from the proximal end of the first arm of the clip assembly to lock the clip assembly in the closed configuration.

9. The apparatus of claim 8, wherein the locking feature at the proximal end of the first arm of the clip assembly is formed as a hook that, when locked, mechanically interacts with the locking feature of the capsule to prevent the clip assembly from moving distally relative to the capsule.

10. The apparatus of claim 8, wherein the proximal end of the second arm of the clip assembly includes a locking feature positioned to mechanically lock with a locking feature of the capsule when the yoke is separated from the connecting element and the yoke is disengaged from the proximal end of the second arm of the clip assembly to lock the clip assembly in the closed configuration.

11. The apparatus of claim 1, wherein the clip assembly is configured so that, as the clip assembly is moved distally relative to the capsule, the first and second arms of the clip assembly are moved to the expanded configuration as the first and second arms of the clip assembly project further distally from the capsule and the first and second arms of the clip assembly are drawn into the closed configuration as the clip assembly is withdrawn proximally into the capsule.

12. An apparatus for applying clips to tissue, comprising:
a capsule defining a lumen therein and including openings in proximal and distal ends thereof;
a clip assembly received within the lumen of the capsule for movement between a closed configuration in which distal ends of first and second arms of the clip assembly are drawn toward one another and an expanded configuration in which the distal ends of the first and second arms are separated from one another to receive target tissue therebetween;
a control member a distal end of which is releasably coupled to the clip assembly to transmit to the clip assembly forces applied to a proximal end of the control member to move the clip assembly between the closed and expanded configurations by moving the first and second arms of the clip assembly distally out of and proximally into the capsule; and
a separable yoke connecting the control member to the clip assembly, the yoke including first and second yoke arms extending distally from the control member within the capsule on opposite sides of the clip assembly, the clip assembly including a connecting member extending between the first and second yoke arms coupling the yoke to the clip assembly, wherein the yoke engages proximal ends of the first and second clip arms, the first and second yoke arms being configured to be separated from the connecting member when subjected to a predetermined force by the control member to uncouple the control member from the clip assembly.

13. The apparatus of claim 12, further comprising a flexible sheath extending from a proximal portion to a distal end coupled to the capsule, the flexible sheath enclosing the control member therein.

14. The apparatus of claim 13, further comprising a bushing coupled between a distal end of the flexible sheath and the proximal end of the capsule, the bushing being releasably coupled to the capsule and fixed to the flexible sheath.

\* \* \* \* \*